US011602434B2

(12) United States Patent
Miller et al.

(10) Patent No.: US 11,602,434 B2
(45) Date of Patent: Mar. 14, 2023

(54) SYSTEMS AND METHODS FOR TISSUE ADJUSTMENT

(71) Applicant: Edwards Lifesciences Innovation (Israel) Ltd., Caesarea (IL)

(72) Inventors: Eran Miller, Moshav Beit Elazari (IL); Uriel Aba Pomerantz, Kfar Sava (IL); Oz Cabiri, Hod Hasharon (IL); Yaron Herman, Givat Ada (IL); Yoseph Weitzman, Tel Aviv-Jaffa (IL); Yosef Gross, Moshav Mazor (IL)

(73) Assignee: Edwards Lifesciences Innovation (Israel) Ltd., Caesarea (IL)

( * ) Notice: Subject to any disclaimer, the term of this patent is extended or adjusted under 35 U.S.C. 154(b) by 366 days.

(21) Appl. No.: 16/701,054

(22) Filed: Dec. 2, 2019

(65) Prior Publication Data

US 2020/0100899 A1 Apr. 2, 2020

Related U.S. Application Data

(63) Continuation of application No. 15/463,656, filed on Mar. 20, 2017, now Pat. No. 10,492,909, which is a
(Continued)

(51) Int. Cl.
*A61F 2/24* (2006.01)
*A61B 17/04* (2006.01)
*A61B 17/00* (2006.01)

(52) U.S. Cl.
CPC ........ *A61F 2/2466* (2013.01); *A61B 17/0401* (2013.01); *A61B 17/0469* (2013.01);
(Continued)

(58) Field of Classification Search
CPC .... A61F 2/2466; A61F 2/2427; A61F 2/2457; A61B 2017/0409; A61B 2017/044
See application file for complete search history.

(56) References Cited

U.S. PATENT DOCUMENTS

| | | | |
|---|---|---|---|
| 3,604,488 A | 9/1971 | Wishart et al. | |
| 3,656,185 A | 4/1972 | Carpentier | |

(Continued)

FOREIGN PATENT DOCUMENTS

| | | |
|---|---|---|
| CN | 113331995 A | 9/2021 |
| EP | 1034753 A1 | 9/2000 |

(Continued)

OTHER PUBLICATIONS

Agarwal et al. International Cardiology Perspective Functional Tricuspid Regurgitation, Circ Cardiovasc Interv 2009;2;2;565-573 (2009).

(Continued)

*Primary Examiner* — Alexander J Orkin
(74) *Attorney, Agent, or Firm* — Thomas C. Richardson

(57) ABSTRACT

Apparatus is provided, including an implant including a tissue-adjusting member including a longitudinal member, and a tissue anchor coupled to the tissue-adjusting member and configured to be anchored into the tissue of the patient. A tissue-coupling element is coupled to the longitudinal member. A delivery tool is reversibly couplable to the implant and is configured to deliver the implant to the tissue of the patient. The delivery tool includes an elongate shaft, a tissue-coupling-element holder coupled to a portion of the elongate shaft, the tissue-coupling-element holder being configured to hold the tissue-coupling element during delivery of the implant to the tissue of the patient, and an actuating element configured to rotate the tissue anchor so as to facilitate anchoring of the tissue anchor into the tissue of the patient while not rotating the tissue-coupling-element holder with respect to the shaft.

19 Claims, 5 Drawing Sheets

Related U.S. Application Data continuation of application No. 14/246,417, filed on Apr. 7, 2014, now Pat. No. 9,622,861, which is a continuation of application No. 12/926,673, filed on Dec. 2, 2010, now Pat. No. 8,734,467.

(60) Provisional application No. 61/265,936, filed on Dec. 2, 2009.

(52) U.S. Cl.
CPC .......... *A61F 2/2427* (2013.01); *A61F 2/2457* (2013.01); *A61B 2017/00243* (2013.01); *A61B 2017/044* (2013.01); *A61B 2017/048* (2013.01); *A61B 2017/0409* (2013.01); *A61B 2017/0414* (2013.01); *A61B 2017/0441* (2013.01); *A61B 2017/0464* (2013.01)

(56) References Cited

U.S. PATENT DOCUMENTS

| | | |
|---|---|---|
| 3,840,018 A | 10/1974 | Heifetz |
| 3,881,366 A | 5/1975 | Bradley et al. |
| 3,898,701 A | 8/1975 | La Russa |
| 4,042,979 A | 8/1977 | Angell |
| 4,118,805 A | 10/1978 | Reimels |
| 4,214,349 A | 7/1980 | Munch |
| 4,261,342 A | 4/1981 | Aranguren Duo |
| 4,290,151 A | 9/1981 | Massana |
| 4,434,828 A | 3/1984 | Trincia |
| 4,473,928 A | 10/1984 | Johnson |
| 4,602,911 A | 7/1986 | Ahmadi et al. |
| 4,625,727 A | 12/1986 | Leiboff |
| 4,712,549 A | 12/1987 | Peters et al. |
| 4,778,468 A | 10/1988 | Hunt et al. |
| 4,917,698 A | 4/1990 | Carpentier et al. |
| 4,935,027 A | 6/1990 | Yoon |
| 4,961,738 A | 10/1990 | Mackin |
| 5,042,707 A | 8/1991 | Taheri |
| 5,061,277 A | 10/1991 | Carpentier et al. |
| 5,064,431 A | 11/1991 | Gilbertson et al. |
| 5,104,407 A | 4/1992 | Lam et al. |
| 5,108,420 A | 4/1992 | Marks |
| 5,201,880 A | 4/1993 | Wright et al. |
| 5,258,008 A | 11/1993 | Wilk |
| 5,300,034 A | 4/1994 | Behnke et al. |
| 5,325,845 A | 7/1994 | Adair |
| 5,346,498 A | 9/1994 | Greelis et al. |
| 5,383,852 A | 1/1995 | Stevens-Wright |
| 5,449,368 A | 9/1995 | Kuzmak |
| 5,450,860 A | 9/1995 | O'Connor |
| 5,464,404 A | 11/1995 | Abela et al. |
| 5,474,518 A | 12/1995 | Farrer Velazquez |
| 5,477,856 A | 12/1995 | Lundquist |
| 5,593,424 A | 1/1997 | Northrup, III |
| 5,601,572 A | 2/1997 | Middleman et al. |
| 5,626,609 A | 5/1997 | Zvenyatsky et al. |
| 5,643,317 A | 7/1997 | Pavcnik et al. |
| 5,669,919 A | 9/1997 | Sanders et al. |
| 5,676,653 A | 10/1997 | Taylor et al. |
| 5,683,402 A | 11/1997 | Cosgrove et al. |
| 5,702,397 A | 12/1997 | Goble et al. |
| 5,702,398 A | 12/1997 | Tarabishy |
| 5,709,695 A | 1/1998 | Northrup, III |
| 5,716,370 A | 2/1998 | Williamson, IV et al. |
| 5,716,397 A | 2/1998 | Myers |
| 5,728,116 A | 3/1998 | Rosenman |
| 5,730,150 A | 3/1998 | Peppel et al. |
| 5,749,371 A | 5/1998 | Zadini et al. |
| 5,752,963 A * | 5/1998 | Allard ............... A61B 17/0401 606/139 |
| 5,782,844 A | 7/1998 | Yoon et al. |
| 5,782,862 A * | 7/1998 | Bonutti ............ A61B 17/0401 606/104 |
| 5,810,882 A | 9/1998 | Bolduc et al. |
| 5,824,066 A | 10/1998 | Gross |
| 5,830,221 A | 11/1998 | Stein et al. |
| 5,843,120 A | 12/1998 | Israel et al. |
| 5,855,614 A | 1/1999 | Stevens et al. |
| 5,876,373 A | 3/1999 | Giba et al. |
| 5,935,098 A | 8/1999 | Blaisdell et al. |
| 5,957,953 A | 9/1999 | DiPoto et al. |
| 5,961,440 A | 10/1999 | Schweich, Jr. et al. |
| 5,961,539 A | 10/1999 | Northrup, III et al. |
| 5,984,959 A | 11/1999 | Robertson et al. |
| 5,993,459 A * | 11/1999 | Larsen ............... A61B 17/0469 606/104 |
| 6,042,554 A | 3/2000 | Rosenman et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,074,341 A | 6/2000 | Anderson et al. |
| 6,074,401 A | 6/2000 | Gardiner et al. |
| 6,074,417 A | 6/2000 | Peredo |
| 6,086,582 A | 7/2000 | Altman et al. |
| 6,102,945 A | 8/2000 | Campbell |
| 6,106,550 A | 8/2000 | Magovern et al. |
| 6,110,200 A | 8/2000 | Hinnenkamp |
| 6,132,390 A | 10/2000 | Cookston et al. |
| 6,143,024 A | 11/2000 | Campbell et al. |
| 6,159,240 A | 12/2000 | Sparer et al. |
| 6,165,119 A | 12/2000 | Schweich, Jr. et al. |
| 6,174,332 B1 | 1/2001 | Loch et al. |
| 6,183,411 B1 | 2/2001 | Mortier et al. |
| 6,187,040 B1 | 2/2001 | Wright |
| 6,210,347 B1 | 4/2001 | Forsell |
| 6,217,610 B1 | 4/2001 | Carpentier et al. |
| 6,228,032 B1 | 5/2001 | Eaton et al. |
| 6,231,602 B1 | 5/2001 | Carpentier et al. |
| 6,251,092 B1 | 6/2001 | Qin et al. |
| 6,296,656 B1 | 10/2001 | Bolduc et al. |
| 6,315,784 B1 | 11/2001 | Djurovic |
| 6,319,281 B1 | 11/2001 | Patel |
| 6,328,746 B1 | 12/2001 | Gambale |
| 6,332,893 B1 | 12/2001 | Mortier et al. |
| 6,355,030 B1 | 3/2002 | Aldrich et al. |
| 6,361,559 B1 | 3/2002 | Houser et al. |
| 6,368,348 B1 | 4/2002 | Gabbay |
| 6,402,780 B2 | 6/2002 | Williamson, IV et al. |
| 6,406,420 B1 | 6/2002 | McCarthy et al. |
| 6,406,493 B1 | 6/2002 | Tu et al. |
| 6,419,696 B1 | 7/2002 | Ortiz et al. |
| 6,451,054 B1 | 9/2002 | Stevens |
| 6,458,076 B1 | 10/2002 | Pruitt |
| 6,461,336 B1 | 10/2002 | Larre |
| 6,461,366 B1 | 10/2002 | Seguin |
| 6,470,892 B1 | 10/2002 | Forsell |
| 6,503,274 B1 | 1/2003 | Howanec, Jr. et al. |
| 6,524,338 B1 | 2/2003 | Gundry |
| 6,527,780 B1 | 3/2003 | Wallace et al. |
| 6,530,952 B2 | 3/2003 | Vesely |
| 6,533,772 B1 | 3/2003 | Sherts et al. |
| 6,537,314 B2 | 3/2003 | Langberg et al. |
| 6,547,801 B1 | 4/2003 | Dargent et al. |
| 6,554,845 B1 | 4/2003 | Fleenor et al. |
| 6,564,805 B2 | 5/2003 | Garrison et al. |
| 6,565,603 B2 | 5/2003 | Cox |
| 6,569,198 B1 | 5/2003 | Wilson et al. |
| 6,579,297 B2 | 6/2003 | Bicek et al. |
| 6,589,160 B2 | 7/2003 | Schweich, Jr. et al. |
| 6,592,593 B1 | 7/2003 | Parodi et al. |
| 6,602,288 B1 | 8/2003 | Cosgrove et al. |
| 6,602,289 B1 | 8/2003 | Colvin et al. |
| 6,613,078 B1 | 9/2003 | Barone |
| 6,613,079 B1 | 9/2003 | Wolinsky et al. |
| 6,619,291 B2 | 9/2003 | Hlavka et al. |
| 6,626,899 B2 | 9/2003 | Houser et al. |
| 6,626,917 B1 | 9/2003 | Craig |
| 6,626,930 B1 | 9/2003 | Allen et al. |
| 6,629,534 B1 | 10/2003 | St. Goar et al. |
| 6,629,921 B1 | 10/2003 | Schweich, Jr. et al. |
| 6,651,671 B1 | 11/2003 | Donlon et al. |
| 6,652,556 B1 | 11/2003 | VanTassel et al. |
| 6,682,558 B2 | 1/2004 | Tu et al. |

(56) References Cited

U.S. PATENT DOCUMENTS

| | | |
|---|---|---|
| 6,689,125 B1 | 2/2004 | Keith et al. |
| 6,689,164 B1 | 2/2004 | Seguin |
| 6,695,866 B1 | 2/2004 | Kuehn et al. |
| 6,702,826 B2 | 3/2004 | Liddicoat et al. |
| 6,702,846 B2 | 3/2004 | Mikus et al. |
| 6,706,065 B2 | 3/2004 | Langberg et al. |
| 6,709,385 B2 | 3/2004 | Forsell |
| 6,709,456 B2 | 3/2004 | Langberg et al. |
| 6,711,444 B2 | 3/2004 | Koblish |
| 6,719,786 B2 | 4/2004 | Ryan et al. |
| 6,723,038 B1 | 4/2004 | Schroeder et al. |
| 6,726,716 B2 | 4/2004 | Marquez |
| 6,726,717 B2 | 4/2004 | Alfieri et al. |
| 6,749,630 B2 | 6/2004 | McCarthy et al. |
| 6,752,813 B2 | 6/2004 | Goldfarb et al. |
| 6,764,310 B1 | 7/2004 | Ichihashi et al. |
| 6,764,510 B2 | 7/2004 | Vidlund et al. |
| 6,764,810 B2 | 7/2004 | Ma et al. |
| 6,770,083 B2 | 8/2004 | Seguin |
| 6,786,924 B2 | 9/2004 | Ryan et al. |
| 6,786,925 B1 | 9/2004 | Schoon et al. |
| 6,790,231 B2 | 9/2004 | Liddicoat et al. |
| 6,797,001 B2 | 9/2004 | Mathis et al. |
| 6,797,002 B2 | 9/2004 | Spence et al. |
| 6,802,319 B2 | 10/2004 | Stevens et al. |
| 6,805,710 B2 | 10/2004 | Bolling et al. |
| 6,805,711 B2 | 10/2004 | Quijano et al. |
| 6,855,126 B2 | 2/2005 | Baugh |
| 6,858,039 B2 | 2/2005 | McCarthy |
| 6,884,250 B2 | 4/2005 | Monassevitch et al. |
| 6,893,459 B1 | 5/2005 | Macoviak |
| 6,908,478 B2 | 6/2005 | Alferness et al. |
| 6,908,482 B2 | 6/2005 | McCarthy et al. |
| 6,918,917 B1 | 7/2005 | Nguyen et al. |
| 6,926,730 B1 | 8/2005 | Nguyen et al. |
| 6,960,217 B2 | 11/2005 | Bolduc |
| 6,976,995 B2 | 12/2005 | Mathis et al. |
| 6,986,775 B2 | 1/2006 | Morales et al. |
| 6,989,028 B2 | 1/2006 | Lashinski et al. |
| 6,997,951 B2 | 2/2006 | Solem et al. |
| 7,004,176 B2 | 2/2006 | Lau |
| 7,007,798 B2 | 3/2006 | Happonen et al. |
| 7,011,669 B2 | 3/2006 | Kimblad |
| 7,011,682 B2 | 3/2006 | Lashinski et al. |
| 7,018,406 B2 | 3/2006 | Seguin et al. |
| 7,037,334 B1 | 5/2006 | Hlavka et al. |
| 7,077,850 B2 | 7/2006 | Kortenbach |
| 7,077,862 B2 | 7/2006 | Vidlund et al. |
| 7,087,064 B1 | 8/2006 | Hyde |
| 7,101,395 B2 | 9/2006 | Tremulis et al. |
| 7,101,396 B2 | 9/2006 | Artof et al. |
| 7,112,207 B2 | 9/2006 | Allen et al. |
| 7,118,595 B2 | 10/2006 | Ryan et al. |
| 7,125,421 B2 | 10/2006 | Tremulis et al. |
| 7,150,737 B2 | 12/2006 | Purdy et al. |
| 7,159,593 B2 | 1/2007 | McCarthy et al. |
| 7,166,127 B2 | 1/2007 | Spence et al. |
| 7,169,187 B2 | 1/2007 | Datta et al. |
| 7,172,625 B2 | 2/2007 | Shu et al. |
| 7,175,660 B2 | 2/2007 | Cartledge et al. |
| 7,186,262 B2 | 3/2007 | Saadat |
| 7,186,264 B2 | 3/2007 | Liddicoat et al. |
| 7,189,199 B2 | 3/2007 | McCarthy et al. |
| 7,192,443 B2 | 3/2007 | Solem et al. |
| 7,220,277 B2 | 5/2007 | Arru et al. |
| 7,226,467 B2 | 6/2007 | Lucatero et al. |
| 7,226,477 B2 | 6/2007 | Cox |
| 7,226,647 B2 | 6/2007 | Kasperchik et al. |
| 7,229,452 B2 | 6/2007 | Kayan |
| 7,238,191 B2 | 7/2007 | Bachmann |
| 7,288,097 B2 | 10/2007 | Seguin |
| 7,294,148 B2 | 11/2007 | McCarthy |
| 7,311,728 B2 | 12/2007 | Solem et al. |
| 7,311,729 B2 | 12/2007 | Mathis et al. |
| 7,314,485 B2 | 1/2008 | Mathis |
| 7,316,710 B1 | 1/2008 | Cheng et al. |
| 7,329,279 B2 | 2/2008 | Haug et al. |
| 7,329,280 B2 | 2/2008 | Bolling et al. |
| 7,335,213 B1 | 2/2008 | Hyde et al. |
| 7,361,190 B2 | 4/2008 | Shaoulian et al. |
| 7,364,588 B2 | 4/2008 | Mathis et al. |
| 7,377,941 B2 | 5/2008 | Rhee et al. |
| 7,390,329 B2 | 6/2008 | Westra et al. |
| 7,404,824 B1 | 7/2008 | Webler et al. |
| 7,431,692 B2 | 10/2008 | Zollinger et al. |
| 7,442,207 B2 | 10/2008 | Rafiee |
| 7,452,376 B2 | 11/2008 | Lim et al. |
| 7,455,690 B2 | 11/2008 | Cartledge et al. |
| 7,485,142 B2 | 2/2009 | Milo |
| 7,485,143 B2 | 2/2009 | Webler et al. |
| 7,500,989 B2 | 3/2009 | Solem et al. |
| 7,507,252 B2 | 3/2009 | Lashinski et al. |
| 7,510,575 B2 | 3/2009 | Spenser et al. |
| 7,510,577 B2 | 3/2009 | Moaddeb et al. |
| 7,527,647 B2 | 5/2009 | Spence |
| 7,530,995 B2 | 5/2009 | Quijano et al. |
| 7,549,983 B2 | 6/2009 | Roue et al. |
| 7,559,936 B2 | 7/2009 | Levine |
| 7,562,660 B2 | 7/2009 | Saadat |
| 7,563,267 B2 | 7/2009 | Goldfarb et al. |
| 7,563,273 B2 | 7/2009 | Goldfarb et al. |
| 7,569,062 B1 | 8/2009 | Kuehn et al. |
| 7,585,321 B2 | 9/2009 | Cribier |
| 7,588,582 B2 | 9/2009 | Starksen et al. |
| 7,591,826 B2 | 9/2009 | Alferness et al. |
| 7,604,646 B2 | 10/2009 | Goldfarb et al. |
| 7,608,091 B2 | 10/2009 | Goldfarb et al. |
| 7,608,103 B2 | 10/2009 | McCarthy |
| 7,618,449 B2 | 11/2009 | Tremulis et al. |
| 7,625,403 B2 | 12/2009 | Krivoruchko |
| 7,632,303 B1 | 12/2009 | Stalker et al. |
| 7,635,329 B2 | 12/2009 | Goldfarb et al. |
| 7,635,386 B1 | 12/2009 | Gammie |
| 7,655,015 B2 | 2/2010 | Goldfarb et al. |
| 7,666,204 B2 | 2/2010 | Thornton et al. |
| 7,682,319 B2 | 3/2010 | Martin et al. |
| 7,682,369 B2 | 3/2010 | Seguin |
| 7,686,822 B2 | 3/2010 | Shayani |
| 7,699,892 B2 | 4/2010 | Rafiee et al. |
| 7,704,269 B2 | 4/2010 | St. Goar et al. |
| 7,704,277 B2 | 4/2010 | Zakay et al. |
| 7,722,666 B2 | 5/2010 | Lafontaine |
| 7,736,388 B2 | 6/2010 | Goldfarb et al. |
| 7,748,389 B2 | 7/2010 | Salahieh et al. |
| 7,753,924 B2 | 7/2010 | Starksen et al. |
| 7,758,632 B2 | 7/2010 | Hojeibane et al. |
| 7,780,726 B2 | 8/2010 | Seguin |
| 7,871,368 B2 | 1/2011 | Zollinger et al. |
| 7,871,433 B2 | 1/2011 | Lattouf |
| 7,883,475 B2 | 2/2011 | Dupont et al. |
| 7,883,538 B2 | 2/2011 | To et al. |
| 7,892,281 B2 | 2/2011 | Seguin et al. |
| 7,927,370 B2 | 4/2011 | Webler et al. |
| 7,927,371 B2 | 4/2011 | Navia et al. |
| 7,942,927 B2 | 5/2011 | Kaye et al. |
| 7,947,056 B2 | 5/2011 | Griego et al. |
| 7,955,315 B2 | 6/2011 | Feinberg et al. |
| 7,955,377 B2 | 6/2011 | Melsheimer |
| 7,981,152 B1 | 7/2011 | Webler et al. |
| 7,992,567 B2 | 8/2011 | Hiratsuka et al. |
| 7,993,368 B2 | 8/2011 | Gambale et al. |
| 7,993,397 B2 | 8/2011 | Lashinski et al. |
| 8,012,201 B2 | 9/2011 | Lashinski et al. |
| 8,034,103 B2 | 10/2011 | Burriesci et al. |
| 8,052,592 B2 | 11/2011 | Goldfarb et al. |
| 8,057,493 B2 | 11/2011 | Goldfarb et al. |
| 8,062,355 B2 | 11/2011 | Figulla et al. |
| 8,070,804 B2 | 12/2011 | Hyde et al. |
| 8,070,805 B2 | 12/2011 | Vidlund et al. |
| 8,075,616 B2 | 12/2011 | Solem et al. |
| 8,100,964 B2 | 1/2012 | Spence |
| 8,123,801 B2 | 2/2012 | Milo |
| 8,142,493 B2 | 3/2012 | Spence et al. |
| 8,142,495 B2 | 3/2012 | Hasenkam et al. |

(56) References Cited

U.S. PATENT DOCUMENTS

| | | |
|---|---|---|
| 8,142,496 B2 | 3/2012 | Berreklouw |
| 8,147,542 B2 | 4/2012 | Maisano et al. |
| 8,152,844 B2 | 4/2012 | Rao et al. |
| 8,163,013 B2 | 4/2012 | Machold et al. |
| 8,187,299 B2 | 5/2012 | Goldfarb et al. |
| 8,187,324 B2 | 5/2012 | Webler et al. |
| 8,202,315 B2 | 6/2012 | Hlavka et al. |
| 8,206,439 B2 | 6/2012 | Gomez Duran |
| 8,216,302 B2 | 7/2012 | Wilson et al. |
| 8,231,671 B2 | 7/2012 | Kim |
| 8,262,725 B2 | 9/2012 | Subramanian |
| 8,265,758 B2 | 9/2012 | Policker et al. |
| 8,277,502 B2 | 10/2012 | Miller et al. |
| 8,287,584 B2 | 10/2012 | Salahieh et al. |
| 8,287,591 B2 | 10/2012 | Keidar et al. |
| 8,292,884 B2 | 10/2012 | Levine et al. |
| 8,303,608 B2 | 11/2012 | Goldfarb et al. |
| 8,323,334 B2 | 12/2012 | Deem et al. |
| 8,328,868 B2 | 12/2012 | Paul et al. |
| 8,333,777 B2 | 12/2012 | Schaller et al. |
| 8,343,173 B2 | 1/2013 | Starksen et al. |
| 8,343,174 B2 | 1/2013 | Goldfarb et al. |
| 8,343,213 B2 | 1/2013 | Salahieh et al. |
| 8,349,002 B2 | 1/2013 | Milo |
| 8,353,956 B2 | 1/2013 | Miller et al. |
| 8,357,195 B2 | 1/2013 | Kuehn |
| 8,382,829 B1 | 2/2013 | Call et al. |
| 8,388,680 B2 | 3/2013 | Starksen et al. |
| 8,393,517 B2 | 3/2013 | Milo |
| 8,419,825 B2 | 4/2013 | Burgler et al. |
| 8,430,926 B2 | 4/2013 | Kirson |
| 8,449,573 B2 | 5/2013 | Chu |
| 8,449,599 B2 | 5/2013 | Chau et al. |
| 8,454,686 B2 | 6/2013 | Alkhatib |
| 8,460,370 B2 | 6/2013 | Zakay |
| 8,460,371 B2 | 6/2013 | Hlavka et al. |
| 8,475,491 B2 | 7/2013 | Milo |
| 8,475,525 B2 | 7/2013 | Maisano et al. |
| 8,480,732 B2 | 7/2013 | Subramanian |
| 8,518,107 B2 | 8/2013 | Tsukashima et al. |
| 8,523,940 B2 | 9/2013 | Richardson et al. |
| 8,551,161 B2 | 10/2013 | Dolan |
| 8,585,755 B2 | 11/2013 | Chau et al. |
| 8,591,576 B2 | 11/2013 | Hasenkam et al. |
| 8,608,797 B2 | 12/2013 | Gross et al. |
| 8,628,569 B2 | 1/2014 | Benichou et al. |
| 8,628,571 B1 | 1/2014 | Hacohen et al. |
| 8,641,727 B2 | 2/2014 | Starksen et al. |
| 8,652,202 B2 | 2/2014 | Alon et al. |
| 8,652,203 B2 | 2/2014 | Quadri et al. |
| 8,679,174 B2 | 3/2014 | Ottma et al. |
| 8,685,086 B2 | 4/2014 | Navia et al. |
| 8,728,097 B1 | 5/2014 | Sugimoto et al. |
| 8,728,155 B2 | 5/2014 | Montorfano et al. |
| 8,734,467 B2 | 5/2014 | Miller et al. |
| 8,734,699 B2 | 5/2014 | Heideman et al. |
| 8,740,920 B2 | 6/2014 | Goldfarb et al. |
| 8,747,463 B2 | 6/2014 | Fogarty et al. |
| 8,778,021 B2 | 7/2014 | Cartledge |
| 8,784,481 B2 | 7/2014 | Alkhatib et al. |
| 8,790,367 B2 | 7/2014 | Nguyen et al. |
| 8,790,394 B2 | 7/2014 | Miller et al. |
| 8,795,298 B2 | 8/2014 | Hernlund et al. |
| 8,795,355 B2 | 8/2014 | Alkhatib |
| 8,795,356 B2 | 8/2014 | Quadri et al. |
| 8,795,357 B2 | 8/2014 | Yohanan et al. |
| 8,808,366 B2 | 8/2014 | Braido et al. |
| 8,808,368 B2 | 8/2014 | Maisano et al. |
| 8,845,717 B2 | 9/2014 | Khairkhahan et al. |
| 8,845,723 B2 | 9/2014 | Spence et al. |
| 8,852,261 B2 | 10/2014 | White |
| 8,852,272 B2 | 10/2014 | Gross et al. |
| 8,858,623 B2 | 10/2014 | Miller et al. |
| 8,864,822 B2 | 10/2014 | Spence et al. |
| 8,870,948 B1 | 10/2014 | Erzberger et al. |
| 8,870,949 B2 | 10/2014 | Rowe |
| 8,888,843 B2 | 11/2014 | Khairkhahan et al. |
| 8,889,861 B2 | 11/2014 | Skead et al. |
| 8,894,702 B2 | 11/2014 | Quadri et al. |
| 8,911,461 B2 | 12/2014 | Traynor et al. |
| 8,911,494 B2 | 12/2014 | Hammer et al. |
| 8,926,696 B2 | 1/2015 | Cabiri et al. |
| 8,926,697 B2 | 1/2015 | Gross et al. |
| 8,932,343 B2 | 1/2015 | Alkhatib et al. |
| 8,932,348 B2 | 1/2015 | Solem et al. |
| 8,940,044 B2 | 1/2015 | Hammer et al. |
| 8,945,211 B2 | 2/2015 | Sugimoto |
| 8,951,285 B2 | 2/2015 | Sugimoto et al. |
| 8,951,286 B2 | 2/2015 | Sugimoto et al. |
| 8,961,595 B2 | 2/2015 | Alkhatib |
| 8,961,602 B2 | 2/2015 | Kovach et al. |
| 8,979,922 B2 | 3/2015 | Jayasinghe et al. |
| 8,992,604 B2 | 3/2015 | Gross et al. |
| 9,005,273 B2 | 4/2015 | Salahieh et al. |
| 9,011,520 B2 | 4/2015 | Miller et al. |
| 9,011,530 B2 | 4/2015 | Reich et al. |
| 9,023,100 B2 | 5/2015 | Quadri et al. |
| 9,072,603 B2 | 7/2015 | Tuval et al. |
| 9,107,749 B2 | 8/2015 | Bobo et al. |
| 9,119,719 B2 | 9/2015 | Zipory et al. |
| 9,125,632 B2 | 9/2015 | Loulmet et al. |
| 9,125,742 B2 | 9/2015 | Yoganathan et al. |
| 9,138,316 B2 | 9/2015 | Bielefeld |
| 9,173,646 B2 | 11/2015 | Fabro |
| 9,180,005 B1 | 11/2015 | Lashinski et al. |
| 9,180,007 B2 | 11/2015 | Reich et al. |
| 9,192,472 B2 | 11/2015 | Gross et al. |
| 9,198,756 B2 | 12/2015 | Aklog et al. |
| 9,226,825 B2 | 1/2016 | Starksen et al. |
| 9,265,608 B2 | 2/2016 | Miller et al. |
| 9,326,857 B2 | 5/2016 | Cartledge et al. |
| 9,414,921 B2 | 8/2016 | Miller et al. |
| 9,427,316 B2 | 8/2016 | Schweich, Jr. et al. |
| 9,474,606 B2 | 10/2016 | Zipory et al. |
| 9,526,613 B2 | 12/2016 | Gross et al. |
| 9,561,104 B2 | 2/2017 | Miller et al. |
| 9,579,090 B1 | 2/2017 | Simms et al. |
| 9,622,861 B2 | 4/2017 | Miller et al. |
| 9,693,865 B2 | 7/2017 | Gilmore et al. |
| 9,730,793 B2 | 8/2017 | Reich et al. |
| 9,788,941 B2 | 10/2017 | Hacohen |
| 9,801,720 B2 | 10/2017 | Gilmore et al. |
| 9,907,547 B2 | 3/2018 | Gilmore et al. |
| 10,368,852 B2 | 8/2019 | Gerhardt et al. |
| 2001/0021874 A1 | 9/2001 | Carpentier et al. |
| 2002/0022862 A1 | 2/2002 | Grafton et al. |
| 2002/0082525 A1 | 6/2002 | Oslund et al. |
| 2002/0087048 A1 | 7/2002 | Brock et al. |
| 2002/0095139 A1 | 7/2002 | Keogh et al. |
| 2002/0103532 A1 | 8/2002 | Langberg et al. |
| 2002/0120292 A1 | 8/2002 | Morgan |
| 2002/0151916 A1 | 10/2002 | Muramatsu et al. |
| 2002/0151970 A1 | 10/2002 | Garrison et al. |
| 2002/0169358 A1 | 11/2002 | Mortier et al. |
| 2002/0177904 A1 | 11/2002 | Huxel et al. |
| 2002/0188301 A1 | 12/2002 | Dallara et al. |
| 2002/0188350 A1 | 12/2002 | Arru et al. |
| 2002/0198586 A1 | 12/2002 | Inoue |
| 2003/0018358 A1* | 1/2003 | Saadat .............. A61F 2/2445 606/232 |
| 2003/0050693 A1 | 3/2003 | Quijano et al. |
| 2003/0078465 A1 | 4/2003 | Pai et al. |
| 2003/0078653 A1 | 4/2003 | Vesely et al. |
| 2003/0105519 A1 | 6/2003 | Fasol et al. |
| 2003/0114901 A1 | 6/2003 | Loeb et al. |
| 2003/0120340 A1 | 6/2003 | Liska et al. |
| 2003/0144657 A1 | 7/2003 | Bowe et al. |
| 2003/0171760 A1 | 9/2003 | Gambale |
| 2003/0199974 A1 | 10/2003 | Lee et al. |
| 2003/0204193 A1 | 10/2003 | Gabriel et al. |
| 2003/0204195 A1 | 10/2003 | Keane et al. |
| 2003/0208208 A1* | 11/2003 | Chu .............. A61B 17/062 606/144 |
| 2003/0229350 A1 | 12/2003 | Kay |

(56) References Cited

U.S. PATENT DOCUMENTS

| | | |
|---|---|---|
| 2003/0229395 A1 | 12/2003 | Cox |
| 2004/0002735 A1 | 1/2004 | Lizard et al. |
| 2004/0010287 A1 | 1/2004 | Bonutti |
| 2004/0019359 A1 | 1/2004 | Worley et al. |
| 2004/0019377 A1 | 1/2004 | Taylor et al. |
| 2004/0024451 A1 | 2/2004 | Johnson et al. |
| 2004/0039442 A1 | 2/2004 | St. Goar et al. |
| 2004/0044350 A1 | 3/2004 | Martin et al. |
| 2004/0059413 A1 | 3/2004 | Argento |
| 2004/0068273 A1 | 4/2004 | Fariss et al. |
| 2004/0111095 A1 | 6/2004 | Gordon et al. |
| 2004/0122514 A1 | 6/2004 | Fogarty et al. |
| 2004/0127982 A1 | 7/2004 | Machold et al. |
| 2004/0133274 A1 | 7/2004 | Webler et al. |
| 2004/0133374 A1 | 7/2004 | Kattan |
| 2004/0138744 A1 | 7/2004 | Lashinski et al. |
| 2004/0138745 A1 | 7/2004 | Macoviak et al. |
| 2004/0148019 A1 | 7/2004 | Vidlund et al. |
| 2004/0148020 A1 | 7/2004 | Vidlund et al. |
| 2004/0148021 A1 | 7/2004 | Cartledge et al. |
| 2004/0176788 A1 | 9/2004 | Opolski |
| 2004/0181287 A1 | 9/2004 | Gellman |
| 2004/0186566 A1 | 9/2004 | Hindrichs et al. |
| 2004/0193191 A1 | 9/2004 | Starksen et al. |
| 2004/0243227 A1 | 12/2004 | Starksen et al. |
| 2004/0260317 A1 | 12/2004 | Bloom et al. |
| 2004/0260344 A1 | 12/2004 | Lyons et al. |
| 2004/0260393 A1 | 12/2004 | Rahdert et al. |
| 2004/0260394 A1 | 12/2004 | Douk et al. |
| 2004/0267358 A1 | 12/2004 | Reitan |
| 2005/0004668 A1 | 1/2005 | Aklog et al. |
| 2005/0010287 A1 | 1/2005 | Macoviak et al. |
| 2005/0010787 A1 | 1/2005 | Tarbouriech |
| 2005/0016560 A1 | 1/2005 | Voughlohn |
| 2005/0049692 A1 | 3/2005 | Numamoto et al. |
| 2005/0055038 A1 | 3/2005 | Kelleher et al. |
| 2005/0055087 A1 | 3/2005 | Starksen |
| 2005/0060030 A1 | 3/2005 | Lashinski et al. |
| 2005/0065601 A1 | 3/2005 | Lee et al. |
| 2005/0070999 A1 | 3/2005 | Spence |
| 2005/0075727 A1 | 4/2005 | Wheatley |
| 2005/0090827 A1 | 4/2005 | Gedebou |
| 2005/0090834 A1 | 4/2005 | Chiang et al. |
| 2005/0096740 A1 | 5/2005 | Langberg et al. |
| 2005/0107871 A1 | 5/2005 | Realyvasquez et al. |
| 2005/0119734 A1 | 6/2005 | Spence et al. |
| 2005/0125002 A1 | 6/2005 | Baran et al. |
| 2005/0125011 A1 | 6/2005 | Spence et al. |
| 2005/0131533 A1 | 6/2005 | Alfieri et al. |
| 2005/0137686 A1 | 6/2005 | Salahieh et al. |
| 2005/0137688 A1 | 6/2005 | Salahieh et al. |
| 2005/0137695 A1 | 6/2005 | Salahieh et al. |
| 2005/0159728 A1 | 7/2005 | Armour et al. |
| 2005/0159810 A1 | 7/2005 | Filsoufi |
| 2005/0171601 A1 | 8/2005 | Cosgrove et al. |
| 2005/0177180 A1 | 8/2005 | Kaganov et al. |
| 2005/0177228 A1 | 8/2005 | Solem et al. |
| 2005/0187568 A1 | 8/2005 | Klenk et al. |
| 2005/0192596 A1 | 9/2005 | Jugenheimer et al. |
| 2005/0203549 A1 | 9/2005 | Realyvasquez |
| 2005/0203606 A1 | 9/2005 | VanCamp |
| 2005/0216039 A1 | 9/2005 | Lederman |
| 2005/0216079 A1 | 9/2005 | MaCoviak |
| 2005/0222665 A1 | 10/2005 | Aranyi |
| 2005/0234481 A1 | 10/2005 | Waller |
| 2005/0240199 A1* | 10/2005 | Martinek ............ A61B 17/0483 606/104 |
| 2005/0245821 A1 | 11/2005 | Govari et al. |
| 2005/0256532 A1 | 11/2005 | Nayak et al. |
| 2005/0267478 A1 | 12/2005 | Corradi et al. |
| 2005/0273138 A1 | 12/2005 | To et al. |
| 2005/0288778 A1 | 12/2005 | Shaoulian et al. |
| 2006/0004442 A1 | 1/2006 | Spenser et al. |
| 2006/0004443 A1 | 1/2006 | Liddicoat et al. |
| 2006/0020326 A9 | 1/2006 | Bolduc et al. |
| 2006/0020327 A1 | 1/2006 | Lashinski et al. |
| 2006/0020333 A1 | 1/2006 | Lashinski et al. |
| 2006/0020336 A1 | 1/2006 | Liddicoat |
| 2006/0025787 A1 | 2/2006 | Morales et al. |
| 2006/0025858 A1 | 2/2006 | Alameddine |
| 2006/0030885 A1 | 2/2006 | Hyde |
| 2006/0041319 A1 | 2/2006 | Taylor et al. |
| 2006/0069429 A1 | 3/2006 | Spence et al. |
| 2006/0074486 A1 | 4/2006 | Liddicoat et al. |
| 2006/0085012 A1 | 4/2006 | Dolan |
| 2006/0095009 A1 | 5/2006 | Lampropoulos et al. |
| 2006/0106423 A1 | 5/2006 | Weisel et al. |
| 2006/0116757 A1 | 6/2006 | Lashinski et al. |
| 2006/0122633 A1 | 6/2006 | To et al. |
| 2006/0129166 A1 | 6/2006 | Lavelle |
| 2006/0142694 A1 | 6/2006 | Bednarek et al. |
| 2006/0149280 A1 | 7/2006 | Harvie et al. |
| 2006/0149368 A1 | 7/2006 | Spence |
| 2006/0161265 A1 | 7/2006 | Levine et al. |
| 2006/0184240 A1 | 8/2006 | Jimenez et al. |
| 2006/0184242 A1 | 8/2006 | Lichtenstein |
| 2006/0195134 A1 | 8/2006 | Crittenden |
| 2006/0206203 A1 | 9/2006 | Yang et al. |
| 2006/0241622 A1 | 10/2006 | Zergiebel |
| 2006/0241656 A1 | 10/2006 | Starksen et al. |
| 2006/0241748 A1 | 10/2006 | Lee et al. |
| 2006/0247763 A1 | 11/2006 | Slater |
| 2006/0259135 A1 | 11/2006 | Navia et al. |
| 2006/0271175 A1 | 11/2006 | Woolfson et al. |
| 2006/0276871 A1 | 12/2006 | Lamson et al. |
| 2006/0282161 A1 | 12/2006 | Huynh et al. |
| 2006/0287661 A1 | 12/2006 | Bolduc et al. |
| 2006/0287716 A1 | 12/2006 | Banbury et al. |
| 2007/0001627 A1 | 1/2007 | Lin et al. |
| 2007/0010800 A1 | 1/2007 | Weitzner et al. |
| 2007/0016287 A1 | 1/2007 | Cartledge et al. |
| 2007/0016288 A1 | 1/2007 | Gurskis et al. |
| 2007/0021781 A1 | 1/2007 | Jervis et al. |
| 2007/0027533 A1 | 2/2007 | Douk |
| 2007/0027536 A1 | 2/2007 | Mihaljevic et al. |
| 2007/0032823 A1 | 2/2007 | Tegg |
| 2007/0038221 A1 | 2/2007 | Fine et al. |
| 2007/0038293 A1 | 2/2007 | St.Goar et al. |
| 2007/0038296 A1 | 2/2007 | Navia et al. |
| 2007/0039425 A1 | 2/2007 | Wang |
| 2007/0049942 A1 | 3/2007 | Hindrichs et al. |
| 2007/0049970 A1 | 3/2007 | Belef et al. |
| 2007/0051377 A1 | 3/2007 | Douk et al. |
| 2007/0055206 A1 | 3/2007 | To et al. |
| 2007/0061010 A1 | 3/2007 | Hauser et al. |
| 2007/0066863 A1 | 3/2007 | Rafiee et al. |
| 2007/0078297 A1 | 4/2007 | Rafiee et al. |
| 2007/0080188 A1 | 4/2007 | Spence et al. |
| 2007/0083168 A1 | 4/2007 | Whiting et al. |
| 2007/0083235 A1 | 4/2007 | Jervis et al. |
| 2007/0100427 A1 | 5/2007 | Perouse |
| 2007/0106328 A1 | 5/2007 | Wardle et al. |
| 2007/0112359 A1 | 5/2007 | Kimura et al. |
| 2007/0112422 A1 | 5/2007 | Dehdashtian |
| 2007/0118151 A1 | 5/2007 | Davidson |
| 2007/0118154 A1 | 5/2007 | Crabtree |
| 2007/0118213 A1* | 5/2007 | Loulmet ............ A61B 17/0401 623/2.1 |
| 2007/0118215 A1 | 5/2007 | Moaddeb |
| 2007/0142907 A1 | 6/2007 | Moaddeb et al. |
| 2007/0162111 A1 | 7/2007 | Fukamachi et al. |
| 2007/0173931 A1 | 7/2007 | Tremulis et al. |
| 2007/0198082 A1 | 8/2007 | Kapadia et al. |
| 2007/0219558 A1 | 9/2007 | Deutsch |
| 2007/0239208 A1 | 10/2007 | Crawford |
| 2007/0244554 A1 | 10/2007 | Rafiee et al. |
| 2007/0244556 A1 | 10/2007 | Rafiee et al. |
| 2007/0255397 A1 | 11/2007 | Ryan et al. |
| 2007/0255400 A1 | 11/2007 | Parravicini et al. |
| 2007/0265491 A1 | 11/2007 | Krag et al. |
| 2007/0270755 A1 | 11/2007 | Von Oepen et al. |
| 2007/0276437 A1 | 11/2007 | Call et al. |
| 2007/0282375 A1 | 12/2007 | Hindrichs et al. |
| 2007/0282429 A1 | 12/2007 | Hauser et al. |

(56) References Cited

U.S. PATENT DOCUMENTS

| | | |
|---|---|---|
| 2007/0295172 A1 | 12/2007 | Swartz |
| 2007/0299424 A1 | 12/2007 | Cumming et al. |
| 2008/0004697 A1 | 1/2008 | Lichtenstein et al. |
| 2008/0027483 A1 | 1/2008 | Cartledge et al. |
| 2008/0027555 A1 | 1/2008 | Hawkins |
| 2008/0035160 A1 | 2/2008 | Woodson et al. |
| 2008/0039935 A1 | 2/2008 | Buch et al. |
| 2008/0051703 A1 | 2/2008 | Thornton et al. |
| 2008/0058595 A1 | 3/2008 | Snoke et al. |
| 2008/0065011 A1 | 3/2008 | Marchand et al. |
| 2008/0065204 A1 | 3/2008 | Macoviak et al. |
| 2008/0071366 A1 | 3/2008 | Tuval et al. |
| 2008/0082132 A1 | 4/2008 | Annest et al. |
| 2008/0086138 A1 | 4/2008 | Stone et al. |
| 2008/0086203 A1 | 4/2008 | Roberts |
| 2008/0091169 A1 | 4/2008 | Heideman et al. |
| 2008/0091257 A1 | 4/2008 | Andreas et al. |
| 2008/0097483 A1 | 4/2008 | Ortiz et al. |
| 2008/0097523 A1 | 4/2008 | Bolduc et al. |
| 2008/0103572 A1 | 5/2008 | Gerber |
| 2008/0140116 A1 | 6/2008 | Bonutti |
| 2008/0167713 A1 | 7/2008 | Bolling |
| 2008/0167714 A1 | 7/2008 | St. Goar et al. |
| 2008/0177380 A1 | 7/2008 | Starksen et al. |
| 2008/0195126 A1 | 8/2008 | Solem |
| 2008/0195200 A1 | 8/2008 | Vidlund et al. |
| 2008/0208265 A1 | 8/2008 | Frazier et al. |
| 2008/0221672 A1 | 9/2008 | Lamphere et al. |
| 2008/0228030 A1 | 9/2008 | Godin |
| 2008/0234729 A1 | 9/2008 | Page et al. |
| 2008/0262480 A1 | 10/2008 | Stabler et al. |
| 2008/0262609 A1 | 10/2008 | Gross et al. |
| 2008/0275300 A1 | 11/2008 | Rothe et al. |
| 2008/0275469 A1 | 11/2008 | Fanton et al. |
| 2008/0275551 A1 | 11/2008 | Alfieri |
| 2008/0281353 A1 | 11/2008 | Aranyi et al. |
| 2008/0281411 A1 | 11/2008 | Berreklouw |
| 2008/0287862 A1 | 11/2008 | Weitzner et al. |
| 2008/0288044 A1 | 11/2008 | Osborne |
| 2008/0288062 A1 | 11/2008 | Andrieu et al. |
| 2008/0294251 A1 | 11/2008 | Annest et al. |
| 2008/0300537 A1 | 12/2008 | Bowman |
| 2008/0300629 A1 | 12/2008 | Surti |
| 2008/0312506 A1 | 12/2008 | Spivey et al. |
| 2009/0024110 A1 | 1/2009 | Heideman et al. |
| 2009/0028670 A1 | 1/2009 | Garcia et al. |
| 2009/0043381 A1 | 2/2009 | Macoviak et al. |
| 2009/0054723 A1 | 2/2009 | Khairkhahan et al. |
| 2009/0054969 A1 | 2/2009 | Salahieh et al. |
| 2009/0062866 A1 | 3/2009 | Jackson |
| 2009/0076586 A1 | 3/2009 | Hauser et al. |
| 2009/0076600 A1 | 3/2009 | Quinn |
| 2009/0082797 A1 | 3/2009 | Fung et al. |
| 2009/0088837 A1 | 4/2009 | Gillinov et al. |
| 2009/0093877 A1 | 4/2009 | Keidar et al. |
| 2009/0099650 A1 | 4/2009 | Bolduc et al. |
| 2009/0105816 A1 | 4/2009 | Olsen et al. |
| 2009/0125102 A1 | 5/2009 | Cartledge et al. |
| 2009/0166913 A1 | 7/2009 | Guo et al. |
| 2009/0171439 A1 | 7/2009 | Nissl |
| 2009/0177266 A1 | 7/2009 | Powell et al. |
| 2009/0177274 A1 | 7/2009 | Scorsin et al. |
| 2009/0187216 A1* | 7/2009 | Schmieding .......... A61F 2/0805 606/232 |
| 2009/0248148 A1 | 10/2009 | Shaolian et al. |
| 2009/0254103 A1 | 10/2009 | Deutsch |
| 2009/0264994 A1 | 10/2009 | Saadat |
| 2009/0287231 A1 | 11/2009 | Brooks et al. |
| 2009/0287304 A1 | 11/2009 | Dahlgren et al. |
| 2009/0299409 A1 | 12/2009 | Coe et al. |
| 2009/0326648 A1 | 12/2009 | Machold et al. |
| 2010/0001038 A1 | 1/2010 | Levin et al. |
| 2010/0010538 A1 | 1/2010 | Juravic et al. |
| 2010/0023118 A1 | 1/2010 | Medlock et al. |
| 2010/0030014 A1 | 2/2010 | Ferrazzi |
| 2010/0030328 A1 | 2/2010 | Seguin et al. |
| 2010/0042147 A1 | 2/2010 | Janovsky et al. |
| 2010/0049213 A1 | 2/2010 | Serina et al. |
| 2010/0063542 A1 | 3/2010 | van der Burg et al. |
| 2010/0063550 A1 | 3/2010 | Felix et al. |
| 2010/0076499 A1 | 3/2010 | McNamara et al. |
| 2010/0094248 A1 | 4/2010 | Nguyen et al. |
| 2010/0094314 A1 | 4/2010 | Hernlund et al. |
| 2010/0106141 A1 | 4/2010 | Osypka et al. |
| 2010/0114180 A1 | 5/2010 | Rock et al. |
| 2010/0121349 A1 | 5/2010 | Meier et al. |
| 2010/0121435 A1 | 5/2010 | Subramanian et al. |
| 2010/0121437 A1 | 5/2010 | Subramanian et al. |
| 2010/0130989 A1 | 5/2010 | Bourque et al. |
| 2010/0130992 A1 | 5/2010 | Machold et al. |
| 2010/0152845 A1 | 6/2010 | Bloom et al. |
| 2010/0161042 A1* | 6/2010 | Maisano ............... A61F 2/2457 623/2.11 |
| 2010/0161043 A1 | 6/2010 | Maisano et al. |
| 2010/0168845 A1 | 7/2010 | Wright |
| 2010/0174358 A1 | 7/2010 | Rabkin et al. |
| 2010/0179574 A1 | 7/2010 | Longoria et al. |
| 2010/0217184 A1 | 8/2010 | Koblish et al. |
| 2010/0217382 A1 | 8/2010 | Chau et al. |
| 2010/0234935 A1 | 9/2010 | Bashir et al. |
| 2010/0249497 A1 | 9/2010 | Peine et al. |
| 2010/0249908 A1 | 9/2010 | Chau et al. |
| 2010/0249915 A1 | 9/2010 | Zhang |
| 2010/0249920 A1 | 9/2010 | Bolling et al. |
| 2010/0262232 A1 | 10/2010 | Annest |
| 2010/0262233 A1 | 10/2010 | He |
| 2010/0280605 A1 | 11/2010 | Hammer et al. |
| 2010/0286628 A1 | 11/2010 | Gross |
| 2010/0298929 A1 | 11/2010 | Thornton et al. |
| 2010/0305475 A1 | 12/2010 | Hinchliffe et al. |
| 2010/0324598 A1 | 12/2010 | Anderson |
| 2011/0004210 A1 | 1/2011 | Johnson et al. |
| 2011/0004298 A1 | 1/2011 | Lee et al. |
| 2011/0009956 A1 | 1/2011 | Cartledge et al. |
| 2011/0011917 A1 | 1/2011 | Loulmet |
| 2011/0026208 A1 | 2/2011 | Utsuro et al. |
| 2011/0029066 A1 | 2/2011 | Gilad et al. |
| 2011/0035000 A1 | 2/2011 | Nieminen et al. |
| 2011/0066231 A1 | 3/2011 | Cartledge et al. |
| 2011/0067770 A1 | 3/2011 | Pederson et al. |
| 2011/0071626 A1 | 3/2011 | Wright et al. |
| 2011/0082538 A1 | 4/2011 | Dahlgren et al. |
| 2011/0087146 A1 | 4/2011 | Ryan et al. |
| 2011/0093002 A1 | 4/2011 | Rucker et al. |
| 2011/0106247 A1 | 5/2011 | Miller et al. |
| 2011/0118832 A1 | 5/2011 | Punjabi |
| 2011/0137410 A1 | 6/2011 | Hacohen |
| 2011/0144703 A1 | 6/2011 | Krause et al. |
| 2011/0202130 A1 | 8/2011 | Cartledge et al. |
| 2011/0208283 A1 | 8/2011 | Rust |
| 2011/0230941 A1 | 9/2011 | Markus |
| 2011/0230961 A1 | 9/2011 | Langer et al. |
| 2011/0238088 A1 | 9/2011 | Bolduc et al. |
| 2011/0257433 A1 | 10/2011 | Walker |
| 2011/0257633 A1 | 10/2011 | Cartledge et al. |
| 2011/0264208 A1 | 10/2011 | Duffy et al. |
| 2011/0276062 A1 | 11/2011 | Bolduc |
| 2011/0288435 A1 | 11/2011 | Christy et al. |
| 2011/0301498 A1 | 12/2011 | Maenhout et al. |
| 2012/0053628 A1 | 3/2012 | Sojka et al. |
| 2012/0065464 A1 | 3/2012 | Ellis et al. |
| 2012/0078355 A1 | 3/2012 | Zipory et al. |
| 2012/0078359 A1 | 3/2012 | Li et al. |
| 2012/0089022 A1 | 4/2012 | House et al. |
| 2012/0089125 A1 | 4/2012 | Scheibe et al. |
| 2012/0095552 A1 | 4/2012 | Spence et al. |
| 2012/0109155 A1 | 5/2012 | Robinson et al. |
| 2012/0150290 A1 | 6/2012 | Gabbay |
| 2012/0158021 A1 | 6/2012 | Morrill |
| 2012/0158023 A1 | 6/2012 | Mitelberg et al. |
| 2012/0179086 A1 | 7/2012 | Shank et al. |
| 2012/0191182 A1 | 7/2012 | Hauser et al. |
| 2012/0226349 A1 | 9/2012 | Tuval et al. |
| 2012/0239142 A1 | 9/2012 | Liu et al. |

(56) References Cited

U.S. PATENT DOCUMENTS

| | | |
|---|---|---|
| 2012/0245604 A1 | 9/2012 | Tegzes |
| 2012/0271198 A1 | 10/2012 | Whittaker et al. |
| 2012/0296349 A1 | 11/2012 | Smith et al. |
| 2012/0296417 A1 | 11/2012 | Hill et al. |
| 2012/0310330 A1 | 12/2012 | Buchbinder et al. |
| 2012/0323313 A1 | 12/2012 | Seguin |
| 2013/0030522 A1 | 1/2013 | Rowe et al. |
| 2013/0046373 A1 | 2/2013 | Cartledge et al. |
| 2013/0053884 A1 | 2/2013 | Roorda |
| 2013/0079873 A1 | 3/2013 | Migliazza et al. |
| 2013/0085529 A1 | 4/2013 | Housman |
| 2013/0090724 A1 | 4/2013 | Subramanian et al. |
| 2013/0096673 A1 | 4/2013 | Hill et al. |
| 2013/0116776 A1 | 5/2013 | Gross et al. |
| 2013/0123910 A1 | 5/2013 | Cartledge et al. |
| 2013/0131791 A1 | 5/2013 | Hlavka et al. |
| 2013/0166017 A1 | 6/2013 | Cartledge et al. |
| 2013/0190863 A1 | 7/2013 | Call et al. |
| 2013/0204361 A1 | 8/2013 | Adams et al. |
| 2013/0226289 A1 | 8/2013 | Shaolian et al. |
| 2013/0226290 A1 | 8/2013 | Yellin et al. |
| 2013/0231701 A1 | 9/2013 | Voss et al. |
| 2013/0268069 A1 | 10/2013 | Zakai et al. |
| 2013/0282059 A1 | 10/2013 | Ketai et al. |
| 2013/0289718 A1 | 10/2013 | Tsukashima et al. |
| 2013/0297013 A1 | 11/2013 | Klima et al. |
| 2013/0304093 A1 | 11/2013 | Serina et al. |
| 2013/0331930 A1 | 12/2013 | Rowe et al. |
| 2014/0067054 A1 | 3/2014 | Chau et al. |
| 2014/0081394 A1 | 3/2014 | Keranen et al. |
| 2014/0088368 A1 | 3/2014 | Park |
| 2014/0088646 A1 | 3/2014 | Wales et al. |
| 2014/0094826 A1 | 4/2014 | Sutherland et al. |
| 2014/0094903 A1 | 4/2014 | Miller et al. |
| 2014/0094906 A1 | 4/2014 | Spence et al. |
| 2014/0114390 A1 | 4/2014 | Tobis et al. |
| 2014/0135799 A1 | 5/2014 | Henderson |
| 2014/0142619 A1 | 5/2014 | Serina et al. |
| 2014/0142695 A1 | 5/2014 | Gross et al. |
| 2014/0148849 A1 | 5/2014 | Serina et al. |
| 2014/0155783 A1 | 6/2014 | Starksen et al. |
| 2014/0163670 A1 | 6/2014 | Alon et al. |
| 2014/0163690 A1 | 6/2014 | White |
| 2014/0188108 A1 | 7/2014 | Goodine et al. |
| 2014/0188140 A1 | 7/2014 | Meier et al. |
| 2014/0188215 A1 | 7/2014 | Hlavka et al. |
| 2014/0194976 A1 | 7/2014 | Starksen et al. |
| 2014/0207231 A1 | 7/2014 | Hacohen et al. |
| 2014/0243859 A1 | 8/2014 | Robinson |
| 2014/0243894 A1 | 8/2014 | Groothuis et al. |
| 2014/0243963 A1 | 8/2014 | Sheps et al. |
| 2014/0251042 A1 | 9/2014 | Asselin et al. |
| 2014/0275757 A1 | 9/2014 | Goodwin et al. |
| 2014/0276648 A1 | 9/2014 | Hammer et al. |
| 2014/0296962 A1 | 10/2014 | Cartledge et al. |
| 2014/0303649 A1 | 10/2014 | Nguyen et al. |
| 2014/0303720 A1 | 10/2014 | Sugimoto et al. |
| 2014/0309661 A1 | 10/2014 | Sheps et al. |
| 2014/0309730 A1 | 10/2014 | Alon et al. |
| 2014/0343668 A1 | 11/2014 | Zipory et al. |
| 2014/0350660 A1 | 11/2014 | Cocks et al. |
| 2014/0379006 A1 | 12/2014 | Sutherland et al. |
| 2015/0018940 A1 | 1/2015 | Quill et al. |
| 2015/0051697 A1 | 2/2015 | Spence et al. |
| 2015/0081014 A1 | 3/2015 | Gross et al. |
| 2015/0094800 A1 | 4/2015 | Chawla |
| 2015/0100116 A1 | 4/2015 | Mohl et al. |
| 2015/0112432 A1 | 4/2015 | Reich et al. |
| 2015/0127097 A1 | 5/2015 | Neumann et al. |
| 2015/0133997 A1 | 5/2015 | Deitch et al. |
| 2015/0182336 A1 | 7/2015 | Zipory et al. |
| 2015/0230919 A1 | 8/2015 | Chau et al. |
| 2015/0272586 A1 | 10/2015 | Herman et al. |
| 2015/0272734 A1 | 10/2015 | Sheps et al. |
| 2015/0282931 A1 | 10/2015 | Brunnett et al. |
| 2015/0351910 A1 | 12/2015 | Gilmore et al. |
| 2016/0008132 A1 | 1/2016 | Cabiri et al. |
| 2016/0029920 A1 | 2/2016 | Kronstrom et al. |
| 2016/0058557 A1 | 3/2016 | Reich et al. |
| 2016/0113767 A1 | 4/2016 | Miller et al. |
| 2016/0120642 A1 | 5/2016 | Shaolian et al. |
| 2016/0120645 A1 | 5/2016 | Alon |
| 2016/0158008 A1 | 6/2016 | Miller et al. |
| 2016/0242762 A1 | 8/2016 | Gilmore et al. |
| 2016/0262755 A1 | 9/2016 | Zipory et al. |
| 2016/0302917 A1 | 10/2016 | Schewel |
| 2016/0317302 A1 | 11/2016 | Madjarov et al. |
| 2016/0361058 A1 | 12/2016 | Bolduc et al. |
| 2016/0361168 A1 | 12/2016 | Gross et al. |
| 2016/0361169 A1 | 12/2016 | Gross et al. |
| 2017/0000609 A1 | 1/2017 | Gross et al. |
| 2017/0042670 A1 | 2/2017 | Shaolian et al. |
| 2017/0100119 A1 | 4/2017 | Baird et al. |
| 2017/0224489 A1 | 8/2017 | Starksen et al. |
| 2017/0245993 A1 | 8/2017 | Gross et al. |
| 2018/0008409 A1 | 1/2018 | Kutzik et al. |
| 2018/0049875 A1 | 2/2018 | Iflah et al. |
| 2018/0140420 A1 | 5/2018 | Hayoz et al. |
| 2018/0168803 A1 | 6/2018 | Pesce et al. |
| 2018/0228608 A1 | 8/2018 | Sheps et al. |
| 2018/0256334 A1 | 9/2018 | Sheps et al. |
| 2018/0289480 A1 | 10/2018 | D'ambra et al. |
| 2018/0318080 A1 | 11/2018 | Quill et al. |
| 2018/0318083 A1 | 11/2018 | Bolling et al. |
| 2019/0029498 A1 | 1/2019 | Mankowski et al. |
| 2019/0038411 A1 | 2/2019 | Alon |
| 2019/0111239 A1 | 4/2019 | Bolduc et al. |
| 2019/0117400 A1 | 4/2019 | Medema et al. |
| 2019/0125325 A1 | 5/2019 | Sheps et al. |
| 2019/0151093 A1 | 5/2019 | Keidar et al. |
| 2019/0175344 A1 | 6/2019 | Khairkhahan |
| 2019/0175345 A1 | 6/2019 | Schaffner et al. |
| 2019/0175346 A1 | 6/2019 | Schaffner et al. |
| 2019/0183648 A1 | 6/2019 | Trapp et al. |
| 2019/0240023 A1 | 8/2019 | Spence et al. |
| 2019/0290260 A1 | 9/2019 | Caffes et al. |
| 2019/0290431 A1 | 9/2019 | Genovese et al. |
| 2019/0321049 A1 | 10/2019 | Herman et al. |
| 2019/0343633 A1 | 11/2019 | Garvin et al. |
| 2020/0015971 A1 | 1/2020 | Brauon et al. |
| 2020/0289267 A1 | 9/2020 | Peleg et al. |
| 2020/0337840 A1 | 10/2020 | Reich |
| 2021/0015475 A1 | 1/2021 | Lau |
| 2021/0059820 A1 | 3/2021 | Clark et al. |
| 2021/0085461 A1 | 3/2021 | Neumark et al. |
| 2021/0093453 A1 | 4/2021 | Peleg et al. |
| 2022/0096232 A1 | 3/2022 | Skaro et al. |

FOREIGN PATENT DOCUMENTS

| | | |
|---|---|---|
| EP | 3531975 A1 | 9/2019 |
| WO | 9205093 A1 | 4/1992 |
| WO | 9846149 A1 | 10/1998 |
| WO | 02085250 A3 | 2/2003 |
| WO | 03047467 A1 | 6/2003 |
| WO | 2010000454 A1 | 1/2010 |
| WO | 2012176195 A3 | 3/2013 |
| WO | 2014064964 A1 | 5/2014 |
| WO | 2019145941 A1 | 8/2019 |
| WO | 2019145947 A1 | 8/2019 |
| WO | 2019182645 A1 | 9/2019 |
| WO | 2019224814 A1 | 11/2019 |
| WO | 2020240282 A2 | 12/2020 |
| WO | 2021014440 A2 | 1/2021 |
| WO | 2021038559 A1 | 3/2021 |
| WO | 2021038560 A1 | 3/2021 |

OTHER PUBLICATIONS

Ahmadi, A., G. Spillner, and Th Johannesson. "Hemodynamic changes following experimental production and correction of acute mitral regurgitation with an adjustable ring prosthesis." The Thoracic and cardiovascular surgeon36.06 (1988): 313-319.

(56) References Cited

OTHER PUBLICATIONS

Ahmadi, Ali et al. "Percutaneously adjustable pulmonary artery band." The Annals of thoracic surgery 60 (1995): S520-S522.
Alfieri et al."Novel Suture Device for Beating-Heart Mitral Leaflet Approximation", Ann Thorac Surg. 2002, 74:1488-1493.
Alfieri et al., "An effective technique to correct anterior mitral leaflet prolapse," J Card 14(6):468-470 (1999).
Alfieri et al., "The double orifice technique in mitral valve repair: a simple solution for complex problems," Journal of Thoracic Cardiovascular Surgery 122:674-681 (2001).
Alfieri, "The edge-to-edge repair of the mitral valve," [Abstract] 6th Annual NewEra Cardiac Care: Innovation & Technology, Heart Surgery Forum pp. 103. (2000).
Amplatzer Cardiac Plug brochure (English pages), AGA Medical Corporation (Plymouth, MN) (copyright 2008-2010, downloaded Jan. 11, 2011).
AMPLATZER® Cribriform Occluder. A patient guide to Percutaneous, Transcatheter, Atrial Septal Defect Closuer, AGA Medical Corporation, Apr. 2008.
AMPLATZER® Septal Occluder. A patient guide to the Non-Surgical Closuer of the Atrial Septal Defect Using the AMPLATZER Septal Occluder System, AGA Medical Corporation, Apr. 2008.
Assad, Renato S. "Adjustable Pulmonary Artery Banding." (2014).
Brennan, Jennifer, 510(k) Summary of safety and effectiveness, Jan. 2008.
Daebritz, S. et al. "Experience with an adjustable pulmonary artery banding device in two cases: initial success-midterm failure." The Thoracic and cardiovascular surgeon 47.01 (1999): 51-52.
Dang NC et al. "Simplified Placement of Multiple Artificial Mitral Valve Chords," The Heart Surgery Forum #2005-1005, 8 (3) (2005).
Dictionary.com definition of "lock", Jul. 29, 2013.
Dieter RS, "Percutaneous valve repair: Update on mitral regurgitation and endovascular approaches to the mitral valve," Applications in Imaging, Cardiac Interventions, Supported by an educational grant from Amersham Health pp. 11-14 (2003).
Elliott, Daniel S., Gerald W. Timm, and David M. Barrett. "An implantable mechanical urinary sphincter: a new nonhydraulic design concept." Urology52.6 (1998): 1151-1154.
Langer et al. Ring plus String: Papillary muscle repositioning as an adjunctive repair technique for ischemic mitral Yegurgitation, The Journal of Thoracic Cardiovascular surgery vol. 133 No. 1, Jan. 2007.
Langer et al. Ring+String, Successful Repair technique for ischemic mitral regurgitation with severe leaflet Tethering, The Department of Thoracic Cardiovascular surgery, Hamburg, Germany, Nov. 2008.
Maisano, "The double-orifice technique as a standardized approach to treat mitral," European Journal of Cardio-thoracic Surgery 17 (2000) 201-205.
O'Reilly S et al., "Heart valve surgery pushes the envelope," Medtech Insight 8(3): 73, 99-108 (2006).
Odell JA et al., "Early Results o4yf a Simplified Method of Mitral Valve Annuloplasty," Circulation 92:150-154 (1995).
Park, Sang C. et al. "A percutaneously adjustable device for banding of the pulmonary trunk." International journal of cardiology 9.4 (1985): 477-484.
Swain CP et al., "An endoscopically deliverable tissue-transfixing device for securing biosensors in the gastrointestinal tract," Gastrointestinal Endoscopy 40(6): 730-734 (1994).
Swenson, O. An experimental implantable urinary sphincter. Invest Urol. Sep. 1976;14(2):100-3.
Swenson, O. and Malinin, T.I., 1978. An improved mechanical device for control of urinary incontinence. Investigative urology, 15(5), pp. 389-391.
Swenson, Orvar. "Internal device for control of urinary incontinence." Journal of pediatric surgery 7.5 (1972): 542-545.
Tajik, Abdul, "Two dimensional real-time ultrasonic imaging of the heart and great vessels", Mayo Clin Proc. vol. 53:271-303, 1978.

* cited by examiner

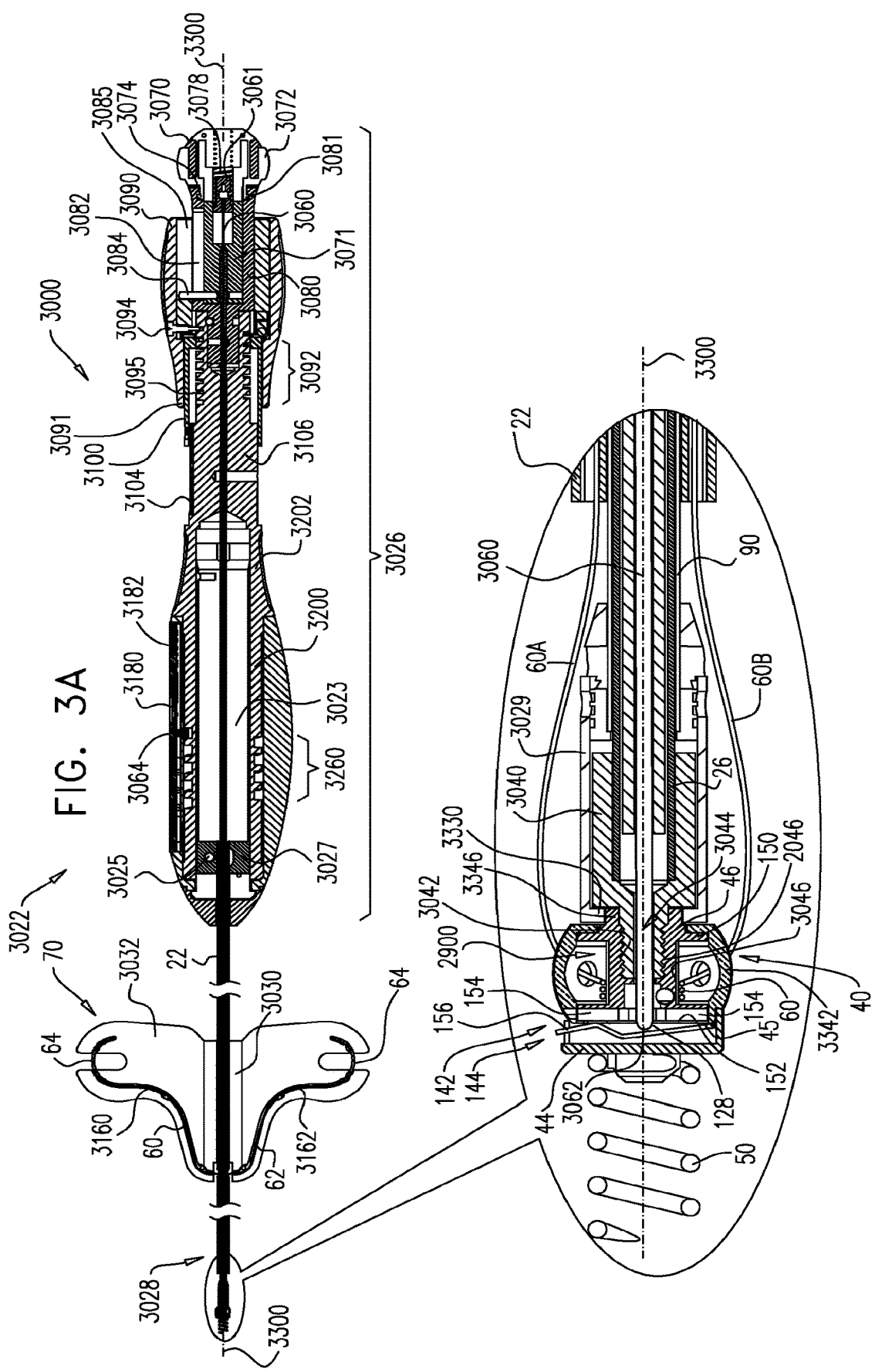

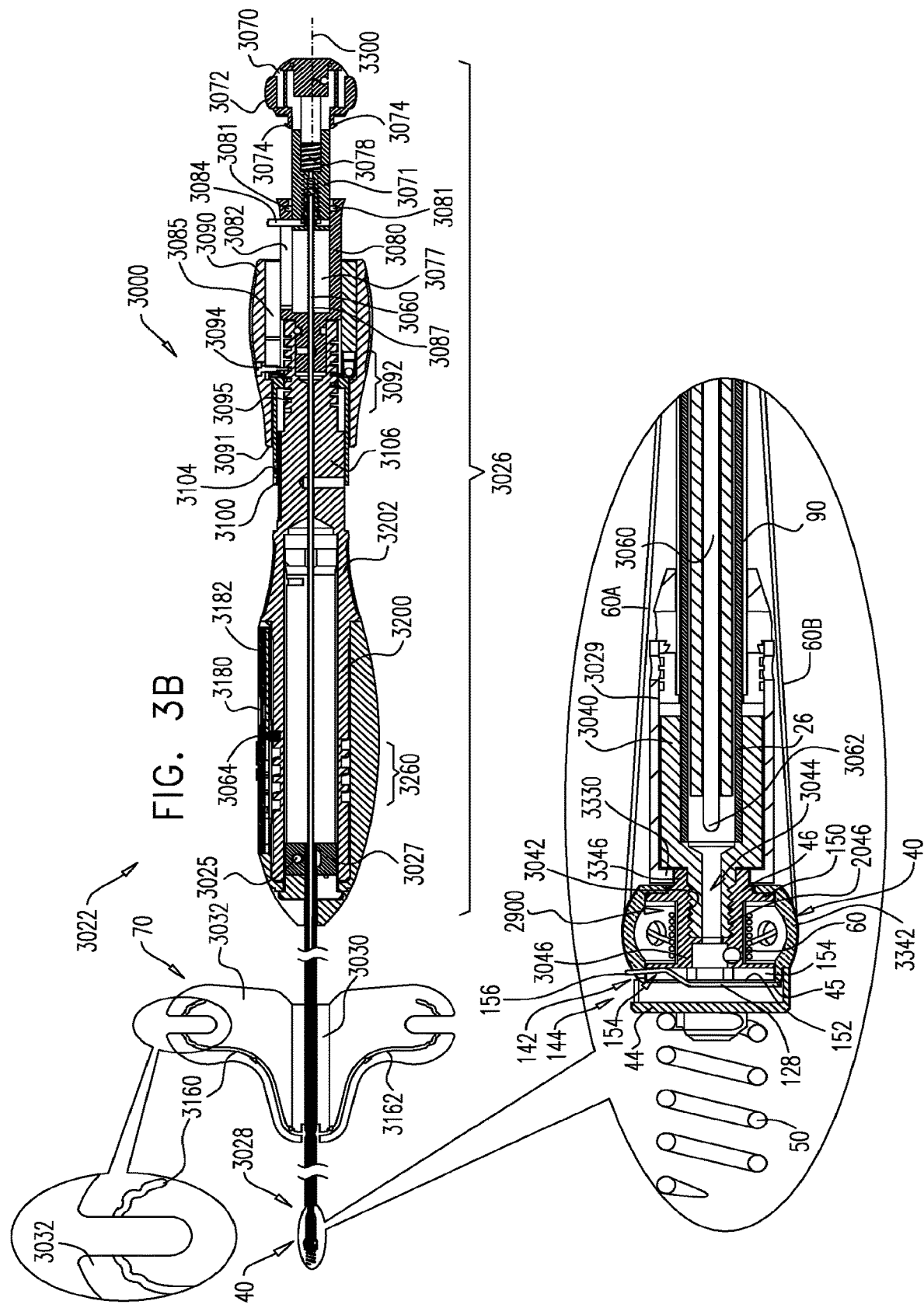

SYSTEMS AND METHODS FOR TISSUE ADJUSTMENT

CROSS-REFERENCES TO RELATED APPLICATIONS

The present application is a continuation of U.S. patent application Ser. No. 15/463,656 to Miller et al., filed Mar. 20, 2017, entitled, "Tool for actuating an adjusting mechanism," which published as US 2017/0209270 and which is a continuation of U.S. patent application Ser. No. 14/246,417 to Miller et al., filed Apr. 7, 2014, entitled, "Tool for actuating an adjusting mechanism," which issued as U.S. Pat. No. 9,622,861, and which is a continuation of U.S. patent application Ser. No. 12/926,673, to Miller et al., filed Dec. 2, 2010, entitled, "Delivery tool for implantation of spool assembly coupled to a helical anchor," which issued as U.S. Pat. No. 8,734,467, and which:

(a) claims priority from U.S. Provisional Application 61/265,936 to Miller et al., filed Dec. 2, 2009, entitled, "Delivery tool for implantation of spool assembly coupled to a helical anchor;" and (b) is related to PCT application PCT/IL2010/001024, entitled, "Delivery tool for implantation of spool assembly coupled to a helical anchor," filed on Dec. 2, 2010, which published as WO 2011/067770.

All of these patents and applications are incorporated herein by reference.

FIELD OF THE INVENTION

The present invention relates in general to valve repair. More specifically, the present invention relates to repair of an atrioventricular valve and a delivery tool therefor.

BACKGROUND

Ischemic heart disease causes mitral regurgitation by the combination of ischemic dysfunction of the papillary muscles, and the dilatation of the left ventricle that is present in ischemic heart disease, with the subsequent displacement of the papillary muscles and the dilatation of the mitral valve annulus.

Dilation of the annulus of the mitral valve prevents the valve leaflets from fully coapting when the valve is closed. Mitral regurgitation of blood from the left ventricle into the left atrium results in increased total stroke volume and decreased cardiac output, and ultimate weakening of the left ventricle secondary to a volume overload and a pressure overload of the left atrium.

U.S. Pat. No. 7,431,692 to Zollinger et al. describes an adjustable support pad for adjustably holding a tensioning line used to apply tension to a body organ. The adjustable support pad can include a locking mechanism for preventing slidable movement of the tensioning element in one or both directions. The locking mechanism may include spring-loaded locks, rotatable cam-like structures, and/or rotatable spool structures. The adjustable support pad may be formed from rigid, semi-rigid, and/or flexible materials, and may be formed to conform to the outer surface of a body organ. The adjustable support pad can be configured to adjustably hold one or more separate tensioning lines, and to provide for independent adjustment of one or more tensioning lines or groups thereof.

US 2007/0118151 to Davidson describes a method and system to achieve leaflet coaptation in a cardiac valve percutaneously by creation of neochordae to prolapsing valve segments. This technique is especially useful in cases of ruptured chordae, but may be utilized in any segment of prolapsing leaflet. The technique described herein has the additional advantage of being adjustable in the beating heart. This allows tailoring of leaflet coaptation height under various loading conditions using image-guidance, such as echocardiography. This offers an additional distinct advantage over conventional open-surgery placement of artificial chordae. In traditional open surgical valve repair, chord length must be estimated in the arrested heart and may or may not be correct once the patient is weaned from cardiopulmonary bypass. The technique described below also allows for placement of multiple artificial chordae, as dictated by the patient's pathophysiology.

U.S. Pat. No. 6,626,930 to Allen et al. describes apparatus and method for the stabilization and fastening of two pieces of tissue. A single device may be used to both stabilize and fasten the two pieces of tissue, or a separate stabilizing device may be used in conjunction with a fastening device. The stabilizing device may comprise a probe with vacuum ports and/or mechanical clamps disposed at the distal end to approximate the two pieces of tissue. After the pieces of tissue are stabilized, they are fastened together using sutures or clips. One exemplary embodiment of a suture-based fastener comprises a toggle and suture arrangement deployed by a needle, wherein the needle enters the front side of the tissue and exits the blind side. In a second exemplary embodiment, the suture-based fastener comprises a needle connected to a suture. The needle enters the blind side of the tissue and exits the front side. The suture is then tied in a knot to secure the pieces of tissue. One example of a clip-based fastener comprises a spring-loaded clip having two arms with tapered distal ends and barbs. The probe includes a deployment mechanism which causes the clip to pierce and lockingly secure the two pieces of tissue.

U.S. Pat. No. 6,629,534 to St. Goar et al. describes methods, devices, and systems are provided for performing endovascular repair of atrioventricular and other cardiac valves in the heart. Regurgitation of an atrioventricular valve, particularly a mitral valve, can be repaired by modifying a tissue structure selected from the valve leaflets, the valve annulus, the valve chordae, and the papillary muscles. These structures may be modified by suturing, stapling, snaring, or shortening, using interventional tools which are introduced to a heart chamber. Preferably, the tissue structures will be temporarily modified prior to permanent modification. For example, opposed valve leaflets may be temporarily grasped and held into position prior to permanent attachment.

U.S. Pat. No. 6,752,813 to Goldfarb et al. describes methods and devices for grasping, and optional repositioning and fixation of the valve leaflets to treat cardiac valve regurgitation, particularly mitral valve regurgitation. Such grasping will typically be atraumatic providing a number of benefits. For example, atraumatic grasping may allow repositioning of the devices relative to the leaflets and repositioning of the leaflets themselves without damage to the leaflets. However, in some cases it may be necessary or desired to include grasping which pierces or otherwise permanently affects the leaflets. In some of these cases, the grasping step includes fixation.

US 2003/0105519 to Fasol et al. describes artificial chordae having a strand member and a first and second pair of sutures at either longitudinal end of the strand member. The artificial chordae is preferably a unitary unit, formed from inelastic flexible material. In one embodiment, the artificial chordae comprises multiple strand members joined together at a joined end. Different sized artificial chordae are provided sized to fit the patient's heart. The appropriately sized artificial chordae is chosen by using a chordae sizing gauge having a shaft and a transverse member, to measure the space within the patient's heart where the artificial chordae is attached.

The following patents and patent application publications may be of interest:
PCT Publication WO 07/136783 to Cartledge et al.
U.S. Pat. No. 5,306,296 to Wright et al.
U.S. Pat. No. 6,569,198 to Wilson et al.
U.S. Pat. No. 6,619,291 to Hlavka et al.
U.S. Pat. No. 6,764,510 to Vidlund et al.
U.S. Pat. No. 7,004,176 to Lau
U.S. Pat. No. 7,101,395 to Tremulis et al.
U.S. Pat. No. 7,175,660 to Cartledge et al.
US 2003/0050693 to Quijano et al
US 2003/0167062 to Gambale et al.
US 2004/0024451 to Johnson et al.
US 2004/0148021 to Cartledge et al.
US 2004/0236419 to Milo
US 2005/0171601 to Cosgrove et al.
US 2005/0216039 to Lederman
US 2005/0288781 to Moaddeb et al.
US 2007/0016287 to Cartledge et al.
US 2007/0080188 to Spence et al.
US 2009/0177266 to Powell et al.
The following articles may be of interest:
O'Reilly S et al., "Heart valve surgery pushes the envelope," Medtech Insight 8(3): 73, 99-108 (2006)
Dieter R S, "Percutaneous valve repair: Update on mitral regurgitation and endovascular approaches to the mitral valve," Applications in Imaging, Cardiac Interventions, Supported by an educational grant from Amersham Health pp. 11-14 (2003)

SUMMARY OF THE INVENTION

In some applications of the present invention, a delivery tool is provided for reversible coupling of a rotatable adjusting mechanism thereto, delivery of the adjusting mechanism to tissue of a patient, and rotation of a rotatable structure of the adjusting mechanism. Typically, the adjusting mechanism is coupled to a tissue anchor and the delivery tool facilitates implantation of the adjusting mechanism in cardiac tissue of the patient. The tool facilitates rotation of the adjusting mechanism in order to implant the tissue anchor, without rotating the rotatable structure of the adjusting mechanism. Typically, the adjusting mechanism is coupled to an implant such as a tissue-adjusting member, e.g., one or more artificial chordae tendineae comprising one or more flexible longitudinal members, and the adjusting mechanism facilitates tightening and loosening of the artificial chordae tendineae. Alternatively, the tissue-adjusting member comprises an annuloplasty ring or a portion of a prosthetic valve. For such applications in which the tissue-adjusting member comprises an annuloplasty ring or at least a portion of a prosthetic valve, the tissue-adjusting member comprises a flexible contracting member that adjusts a dimension of at least a portion of the annuloplasty ring or at least a portion of the prosthetic valve.

Typically, the rotatable structure of the adjusting mechanism is shaped to define proximal and distal openings and a channel extending between the proximal and distal openings. A proximal portion of an inner wall of the rotatable structure that surrounds the channel is shaped to define a threaded portion, e.g., a tapered threaded portion that decreases in diameter from the proximal opening.

Typically, the delivery tool has a distal end which is reversibly couplable to the adjusting mechanism and comprises a manipulator, e.g., a screwdriver tool. The manipulator is shaped to define a threaded portion that screws into the threaded portion of the rotatable structure. The delivery tool comprises an ergonomic proximal handle portion that comprises at least two separate rotating members which control separate functions of the manipulator at the distal end of the tool. A proximal-most first knob rotates the manipulator sufficiently to couple together the respective threaded portions of the manipulator and the rotatable structure. A second knob that is distal to the proximal-most knob facilitates rotation of the manipulator sufficiently to rotate the rotatable structure following the coupling of the manipulator to the rotatable structure. For some applications, the second knob is coupled to a visual indicator which indicates the number of rotations of the screwdriver, and thereby, the number of rotations of the rotatable structure. Rotating the second knob in a first rotational direction rotates the second knob such that it advances distally along a helical rotation path. The distal end of the helical rotation path restricts rotation of the second knob and thereby restricts rotation of the rotatable structure beyond a predetermined amount. A third knob, that is distal to the second knob, facilitates implantation by screwing of a tissue anchor adjusting mechanism in tissue of a patient without rotating the rotatable structure of the adjusting mechanism. Thus, the delivery tool provides a single tool which (1) implants the adjusting mechanism in tissue of the patient by screwing the tissue anchor without rotating the rotatable structure of the adjusting mechanism, and (2) subsequently, but during a single advancement of the delivery tool, facilitates rotation of the rotatable structure of the adjusting mechanism without rotating the tissue anchor.

For some applications, the rotatable structure is coupled to a locking mechanism which restricts rotation of the rotatable structure in a resting state of the locking mechanism. The delivery tool comprises an elongate locking mechanism release rod which is slidable within a lumen of the delivery tool in order to release the locking mechanism from the rotatable structure prior to the rotating of the rotatable structure responsively to the rotation of the second knob.

There is therefore provided, in accordance with some applications of the present invention, apparatus, including:
a tissue-adjusting member configured to be coupled to tissue of a patient;
a rotatable structure that is configured to adjust a tension of the tissue-adjusting member;
a tissue anchor coupled to the tissue-adjusting member and configured to screw into the tissue of the patient; and
a delivery tool reversibly couplable to the rotatable structure, the delivery tool including:
 a first actuating element configured to rotate the tissue anchor so as to facilitate screwing of the tissue anchor into the tissue of the patient while not facilitating rotation of the rotatable structure; and
 a second actuating element configured to rotate the rotatable structure while not facilitating rotation of the tissue anchor.

In some applications of the present invention, the tissue anchor includes a helical tissue anchor.

In some applications of the present invention:
the first actuating element includes a first rotatable knob, the second actuating element includes a second rotatable knob, the delivery tool has a longitudinal axis, and the first and second rotatable knobs are configured to rotate about the longitudinal axis of the delivery tool.

In some applications of the present invention, the apparatus further includes a housing surrounding the rotatable structure, and the tissue anchor is coupled to the housing in a manner in which the rotatable structure and the tissue anchor are disposed along the longitudinal axis of the delivery tool.

In some applications of the present invention, the tissue anchor and the rotatable structure are disposed along the longitudinal axis of the delivery tool.

In some applications of the present invention, the tissue anchor has a tissue-anchor-axis-of-rotation that is along the longitudinal axis of the delivery tool, the rotatable structure has a rotatable-structure-axis-of-rotation that is along the longitudinal axis of the delivery tool, and the tissue-anchor-axis-of-rotation and the rotatable-structure-axis-of-rotation are identical.

In some applications of the present invention, the delivery tool includes a first helical groove and a first pin, and the first pin is mechanically coupled to the first rotatable knob and advanceable within the first helical groove.

In some applications of the present invention, the delivery tool includes a first cylindrical element that is shaped so as to define the first helical groove, and the first rotatable knob is coupled to the first cylindrical element in a manner in which, during rotation of the first rotatable knob, the first cylindrical element is configured to rotate about the longitudinal axis of the delivery tool, and the first helical groove advances helically with respect to the first pin.

In some applications of the present invention, the first pin is coupled to a slidable numerical indicator, and, in response to advancement of the first helical groove helically with respect to the first pin, the first pin is advanceable linearly with respect to the delivery tool so as to indicate a number of rotations of the tissue anchor into the tissue of the patient.

In some applications of the present invention:

the cylindrical element is coupled to a proximal end of an elongate tube, a distal end of the elongate tube is reversibly coupleable to the tissue anchor, and during rotation of the first rotatable knob, the cylindrical element rotates the elongate tube, and in turn, the elongate tube rotates the tissue anchor.

In some applications of the present invention:

the delivery tool further includes a torque-delivering tool reversibly coupleable at a distal end thereof to the rotatable structure, a proximal end of the torque-delivering tool is mechanically coupled to the second rotatable knob, the torque-delivering tool is disposed at least in part within the lumen of the elongate tube, during rotation of the first rotatable knob, the torque-delivering tool is not rotated within the elongate tube, and thus, the rotatable structure is not rotated.

In some applications of the present invention, in response to rotation of the second rotatable knob, the torque-delivering tool is rotatable within the lumen of the elongate tube, and responsively to the rotation of the torque-delivering tool within the lumen of the elongate tool, the torque-delivering tool delivers torque to the rotatable structure in order to rotate the rotatable structure.

In some applications of the present invention, the delivery tool includes a second helical groove and a second pin, and the second pin is mechanically coupled to the second rotatable knob and advanceable within the second helical groove.

In some applications of the present invention, the delivery tool includes a second cylindrical element that is shaped so as to define the second helical groove, and the second rotatable knob is coupled to the second pin in a manner in which, during rotation of the second rotatable knob, the second pin is rotatable about the longitudinal axis of the delivery tool within the second helical groove.

In some applications of the present invention:

the delivery tool further includes a rotator coupled to the distal end of the torque-delivering tool, second knob is mechanically coupled to the rotator and configured to rotate the rotator in response to rotation of the second knob, rotation of the rotator by the second knob rotates the torque-delivering tool, and rotation of the torque-delivering tool rotates the rotatable structure.

In some applications of the present invention, the second pin is coupled to a slidable indicator, and, in response to rotation of the second pin within the second helical groove, the slidable indicator is advanceable linearly with respect to the delivery tool so as to indicate a number of rotations of the rotatable structure.

In some applications of the present invention, the tissue-adjusting member includes one or more artificial chordae tendineae coupled at least in part to the rotatable structure, and rotation of the rotatable structure adjusts a tension of the one or more chordae tendineae.

In some applications of the present invention, the apparatus further includes a housing surrounding the rotatable structure, and the tissue anchor is coupled to the tissue-adjusting member via the housing.

In some applications of the present invention, at least a portion of the one or more chordae tendineae is looped through a portion of the rotatable structure.

In some applications of the present invention, the apparatus further includes a tissue-coupling element, each one of the one or more chordae tendineae has a free end, and the free end is coupled to the tissue-coupling element.

In some applications of the present invention, the delivery tool includes a tissue-coupling element holder, and the at least a portion of the tissue-coupling element is disposable within the tissue-coupling element holder during the screwing of the tissue anchor into the tissue of the patient.

In some applications of the present invention, the rotatable structure includes a spool, and successive portions of the one or more chordae tendineae are configured to be wound around the spool responsively to rotation of the second knob in a first rotational direction, and to be unwound from around the spool responsively to rotation of the second knob in a second rotational direction that is opposite the first rotational direction.

In some applications of the present invention, the delivery tool includes a numerical indicator including a range of numbers configured to indicate a number of times the one or more chordae tendineae are wound around the rotatable structure.

In some applications of the present invention:

prior to the screwing of the tissue anchor, at least a portion of the one or more chordae tendineae is wound around a portion of the rotatable structure, and the numerical indicator includes a range of numbers indicating a number of times the one or more chordae tendineae are wound around the rotatable structure prior to the screwing of the tissue anchor.

In some applications of the present invention, the delivery tool further includes a rotatable-structure-manipulator, and the rotatable-structure-manipulator is coupled to the distal end of the torque-delivering tool.

In some applications of the present invention, a portion of the rotatable structure is shaped so as to define a first threaded portion, a portion of the rotatable-structure-manipulator is shaped so as to define a second threaded portion, and the rotatable-structure-manipulator is reversibly couplable to the rotatable structure when the second threaded portion is screwed with respect to the first threaded portion.

In some applications of the present invention, the rotatable structure:
  includes a first end shaped to define a first opening,
  includes a second end having a lower surface shaped so as to define a second opening of the rotatable structure,
  is shaped so as to define a channel extending from the first opening to the second opening, and
  is shaped so as to define a first coupling at the lower surface of the second end thereof, and the apparatus further includes:
    a mechanical element having a surface coupled to the lower surface of the rotatable structure, the mechanical element being shaped to provide:
      a second coupling configured to engage the first coupling during a resting state of the mechanical element, in a manner that restricts rotation of the rotatable structure, and
      a depressible portion coupled to the protrusion, the depressible portion being disposed in communication with the second opening of the lower surface, and configured to disengage the first and second couplings.

In some applications of the present invention, the delivery tool includes an elongate release rod configured to depress the depressible portion and to release the rotatable structure by disengaging the second coupling from the first coupling.

In some applications of the present invention, the torque-delivering tool is shaped so as to define a torque-delivering tool lumen for slidable passage therethrough of the elongate release rod.

There is further provided, in accordance with some applications of the present invention, a method, including:
  using a delivery tool, advancing toward tissue of a patient, a tissue-adjusting member coupled to a tissue anchor and a rotatable structure that is configured to adjust a tension of the tissue-adjusting member;
  implanting the tissue anchor in the tissue of the patient by screwing the tissue anchor into the tissue by actuating a first actuating element of the delivery tool, while not rotating the rotatable structure; and
  subsequently to the implanting, rotating the rotatable structure by actuating a second actuating element of the delivery tool, while not rotating the tissue anchor.

In some applications of the present invention, the screwing of the tissue anchor and the subsequent rotating of the rotatable structure occur during a single advancing using the delivery tool.

In some applications of the present invention, the screwing of the tissue anchor includes screwing the tissue anchor along an axis of rotation, and rotating the rotatable structure includes rotating the rotating structure along the axis of rotation without moving the delivery tool from the axis of rotation.

In some applications of the present invention, advancing toward the tissue of the patient includes advancing at least a distal portion of the delivery tool into a body cavity of the patient, and the screwing of the tissue anchor and the subsequent rotating of the rotatable structure occur without extracting the distal portion of the delivery tool from within the body cavity.

In some applications of the present invention:
  the tissue-adjusting member includes one or more artificial chordae tendineae,
  implanting the tissue anchor in the tissue includes implanting the tissue anchor in a portion of tissue of a ventricle of a heart of the patient, and
  the method further includes coupling at least one free end of the one or more chordae tendineae to at least one native leaflet of a native atrioventricular valve.

In some applications of the present invention, rotating the rotatable structure includes rotating the rotatable structure subsequently to the coupling to the at least one leaflet of the at least one free end of the one or more chordae tendineae.

In some applications of the present invention, rotating the rotatable structure includes adjusting a tension of the one or more chordae tendineae.

In some applications of the present invention, advancing the tissue-adjusting member includes advancing the tissue-adjusting member in a manner in which a portion of the one or more chordae tendineae is wound around a portion of the rotatable structure, and adjusting a tension of the one or more chordae tendineae includes unwinding the portion of the one or more chordae tendineae from around the rotatable structure subsequently to the coupling to the at least one leaflet of the at least one free end of the one or more chordae tendineae.

In some applications of the present invention, adjusting the tension of the one or more chordae tendineae includes winding successive portions of the one or more chordae tendineae around the rotatable structure by rotating the rotatable structure in a first rotational direction.

In some applications of the present invention, adjusting the tension of the one or more chordae tendineae includes unwinding the successive portions of the one or more chordae tendineae from around the rotatable structure by rotating the rotatable structure in a second rotational direction that is opposite the first rotational direction.

There is additionally provided, in accordance with some applications of the present invention, apparatus, including:
  a rotatable structure having a first end shaped to define a first opening, and a second end shaped to define a second opening and having a lower surface thereof, the rotatable structure being shaped to define:
    a channel extending from the first opening to the second opening, and
    a first coupling at the lower surface of the second end thereof;
  a mechanical element having a surface coupled to the lower surface of the rotatable structure, the mechanical element being shaped to provide:
    a second coupling configured to engage the first coupling during a resting state of the mechanical element, in a manner that restricts rotation of the rotatable structure, and
    a depressible portion coupled to the protrusion, the depressible portion being disposed in communication with the second opening of the lower surface, and configured to disengage the first and second couplings;
  a helical anchor coupled to the rotatable structure; and a delivery tool configured to deliver the rotatable structure to a tissue site of a patient, the delivery tool including:
at least a first rotatable knob;
a torque-delivering tool coupled to the first rotatable knob, the torque-delivering tool being shaped to define a torque-delivering-tool lumen;
a screwdriver head coupled to the torque-delivering tool at a distal end thereof, the screwdriver head being shaped to define a screwdriver head and configured to rotate the rotatable structure in response to toque delivered to the screwdriver head by the torque-delivering tool in response to rotation of the first rotatable knob; and
an elongate tool coupled to the knob at a proximal end, the elongate tool being slidably coupled to the delivery tool and disposed at least in part within the torque-delivering-tool lumen, the elongate tool:
having a proximal end coupled to the first rotatable knob and,
having a distal end thereof being advanceable distally, responsively to a distal pushing of the first rotatable knob, through the screwdriver head lumen and through the channel of the rotatable structure, the distal end of the elongate tool being configured to move the depressible portion in a manner in which the elongate tool disengages the first and second couplings.

There is additionally provided, in accordance with some applications of the present invention, a method, including:
coupling a delivery tool to a rotatable structure by rotating a rotatable knob of the delivery tool and screwing a screwdriver head of the delivery tool to a proximal portion the rotatable structure without rotating the rotatable structure, the rotatable structure having a first end shaped to define a first opening, and a second end shaped to define a second opening and having a lower surface thereof, the rotatable structure being shaped to define a channel extending from the first opening to the second opening, and at least one first coupling at the lower surface of the second end thereof,
subsequently to the coupling, disengaging a second coupling from within the at least one first coupling of the rotatable structure by:
pushing distally the rotatable knob,
pushing distally a distal end of an elongate tool through the channel of the rotatable structure and beyond the second opening of the rotatable structure,
responsively to the pushing distally of the distal end of the elongate tool, moving a depressible portion that is coupled to the second coupling and disposed in communication with the second opening of the lower surface of the rotatable structure; and
subsequently to the disengaging, rotating the rotatable structure by rotating at least a portion of the delivery tool.

There is further provided, in accordance with some applications of the present invention, apparatus for adjusting at least one dimension of an implant, including:
a rotatable structure having a first end shaped to define a first opening, and a second end shaped to define a second opening and having a lower surface thereof, the rotatable structure being shaped to define:
a channel extending from the first opening to the second opening, the channel being configured for passage therethrough of an elongate tool, and
at least one first coupling at the lower surface of the second end thereof; and a mechanical element having a surface coupled to the lower surface of the rotatable structure, the mechanical element being shaped to provide:
a second coupling configured to engage the first coupling during a resting state of the mechanical element, in a manner that restricts rotation of the rotatable structure, and
a depressible portion coupled to the protrusion, the depressible portion being disposed in communication with the second opening of the lower surface, and configured to disengage the at least one first coupling and the second coupling in response to a force applied thereto by the elongate tool.

There is also provided, in accordance with some applications of the present invention, a method, including:
providing a rotatable structure, and a mechanical locking element that is coupled to a lower surface of the rotatable structure;
implanting the rotatable structure in cardiac tissue;
advancing an elongate tool through a channel provided by the rotatable structure;
unlocking the rotatable structure from the mechanical locking element by pushing a depressible portion of the locking element;
responsively to the pushing of the depressible portion, dislodging a first coupling provided by the rotatable structure from a second coupling provided by the mechanical element; and
in response to the dislodging, rotating the rotatable structure.

The present invention will be more fully understood from the following detailed description of embodiments thereof, taken together with the drawings, in which:

BRIEF DESCRIPTION OF THE DRAWINGS

FIGS. 3A-B are schematic cross-sectional illustrations of the delivery tool of FIG. 1, in accordance with some applications of the present invention.

DETAILED DESCRIPTION OF THE DRAWINGS

Figure 1:
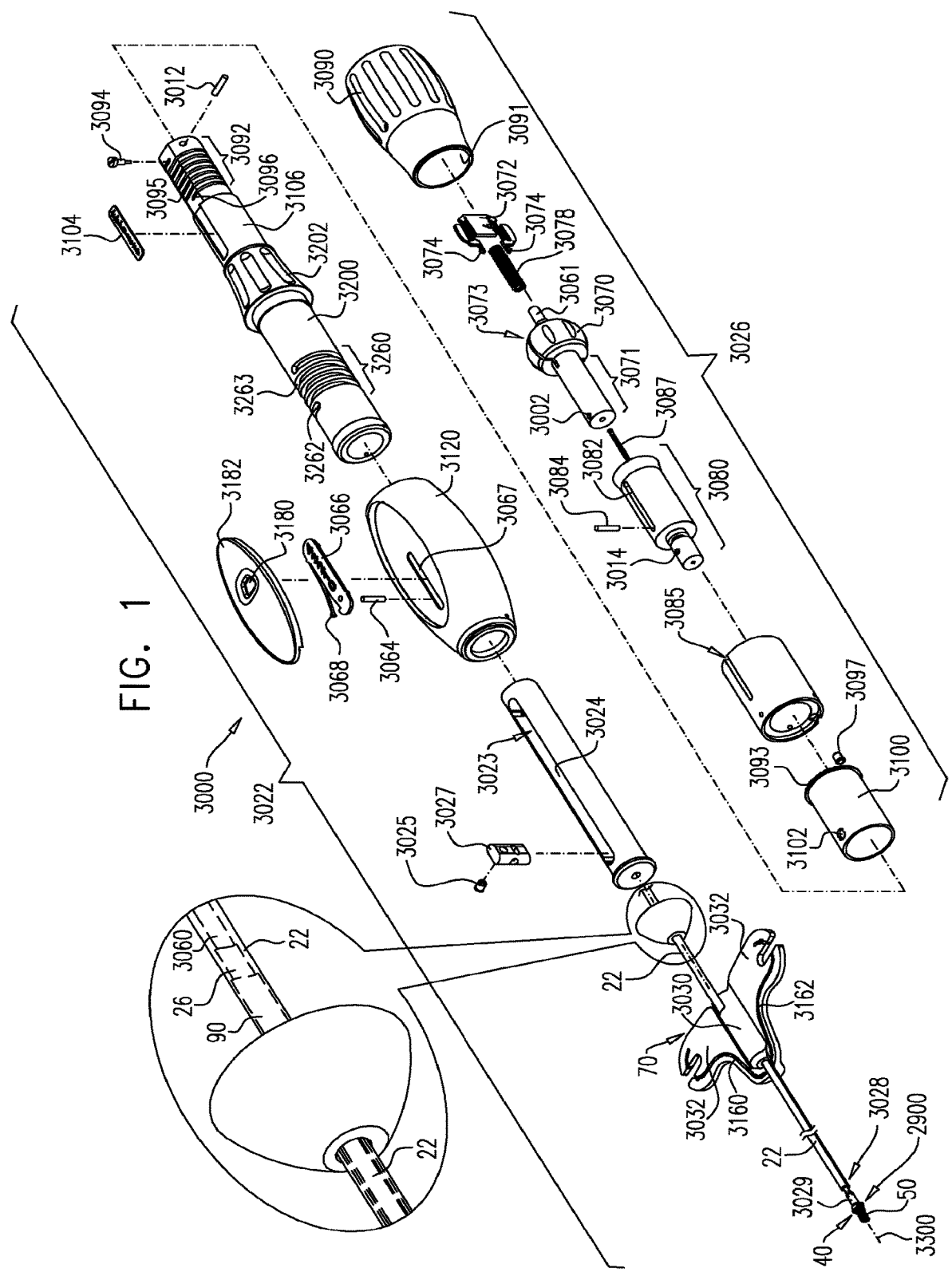
FIG. 1 is a schematic illustration of a delivery tool which facilitates implantation and rotation of a rotatable structure in an adjusting mechanism, in accordance with some applications of the present invention.
Figure 2:
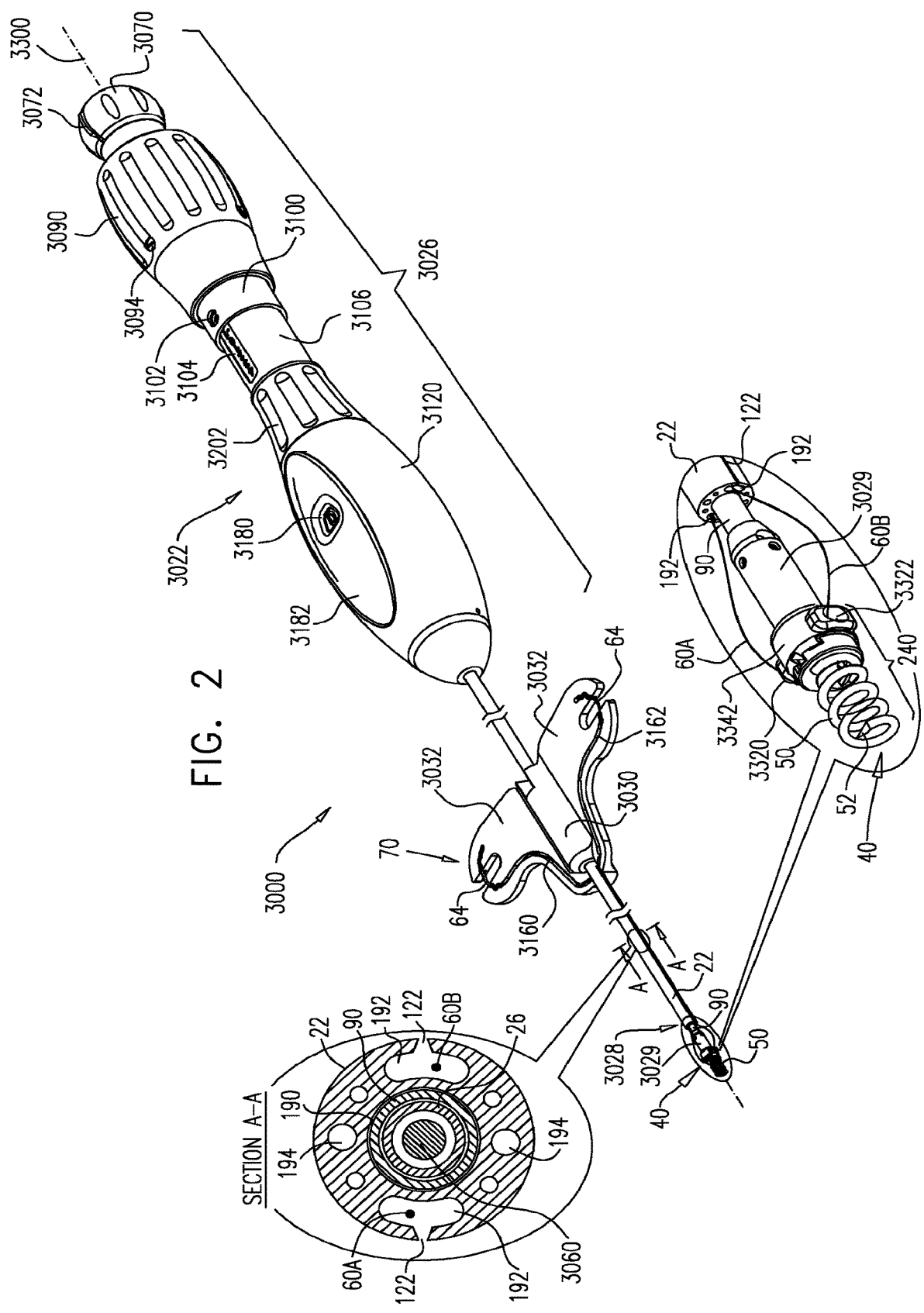
FIG. 2 is a schematic illustration of the delivery tool of FIG. 1 coupled to the adjusting mechanism, in accordance with some applications of the present invention.

Reference is made to FIGS. 1 and 2. FIG. 1 is a schematic illustration of a system 3000 comprising a delivery tool 3022 for (1) delivering and implanting a tissue anchor and an adjusting mechanism 40 coupled thereto, mechanism 40 comprising a rotatable structure 2900, e.g., a spool 3046, to tissue of a patient, and (2) facilitating rotation of the rotatable structure, in accordance with some applications of the present invention. FIG. 2 shows delivery tool 3022 coupled at a distal portion 3028 thereof to adjusting mechanism 40 and artificial chordae tendineae comprising respective portions 60A and 60B of a tissue-adjusting member (e.g., flexible longitudinal member 60), in accordance with some applications of the present invention. Typically, the longitudinal member is looped through the spool of rotatable structure 2900 and defines portions 60A and 60B of member 60. It is to be noted that although the spool of rotatable structure 2900 is described herein as being coupled to one flexible longitudinal member, the spool may be coupled to any number of longitudinal members which function as artificial chordae tendineae.

FIG. 1 is an exploded view of tool 3022 showing the relationship of its components. Tool 3022 has an elongate shaft 22 and a proximal handle portion 3026. For some applications, and as shown herein, shaft 22 comprises a multilumen shaft, by way of illustration and not limitation. For some applications, shaft 22 may be shaped to define only a single central lumen for passage therethrough of a torque-delivering tool 26. Typically, shaft 22 is sized for open-heart and/or minimally-invasive procedures and comprises a flexible material (e.g., a plastic or a plurality of strands of flexible metal such as stainless steel that are bundled together) which may be bent to a desired angle. For some applications shaft 22 is sized for transluminal, percutaneous, or endovascular procedures for delivery of adjusting mechanism 40 coupled to portions 60A and 60B of flexible longitudinal member 60 (labeled in FIG. 2), as described herein.

(In this context, in the specification and in the claims, "proximal" means closer to the orifice through which system 3000 is originally placed into the body of the patient, and "distal" means further from this orifice.)

Proximal handle portion 3026 is shaped to define an ergonomic hand-grasping portion 3120 for the physician to grasp and thereby hold tool 3022. A proximal end portion of shaft 22 is coupled to handle portion 3026, such as by being disposed within a lumen of handle portion 3026.

A distal end portion 3028 of shaft 22 is coupled to, e.g., welded to, an adjusting mechanism holder 3029 having a distal end that is reversibly coupled to adjusting mechanism 40, such as to a proximal portion of a housing 3342 (labeled in FIG. 2) surrounding the rotatable structure of adjusting mechanism 40, described hereinbelow with reference to FIG. 2. Shaft 22 is shaped to define a central lumen through which torque-delivering tool 26 passes. A proximal end of torque-delivering tool 26 is coupled to the rotating mechanism at proximal handle portion 3026. Shaft 22 is shaped to define a central lumen through which torque-delivering tool 26 passes.

Reference is again made to FIG. 2, which shows distal portion 3028 of tool 3022 coupled to adjusting mechanism 40. For some applications, adjusting mechanism 40 comprises rotatable structure housing 3342 which houses rotatable structure 2900. Housing 3342 is coupled at a distal end portion thereof to a tissue anchor 50. Anchor 50 has a pointed distal tip 52 for penetrating cardiac tissue, thereby coupling the anchor to the tissue. Housing 3342 and anchor 50 collectively define a spool assembly 240. Tissue anchor 50 is shown as a helical anchor by way of illustration and not limitation, and may instead be spiral (e.g., having the shape of a corkscrew), shaped so as to define a screw thread, or have another shape that facilitates coupling of the anchor to cardiac tissue upon rotation of the anchor. Alternatively or additionally, anchor 50 may comprise staples, clips, spring-loaded anchors, or other tissue anchors known in the art. For some applications, rotatable structure 2900 comprises a spool (i.e., spool 3046, as shown hereinbelow in FIGS. 3A-B), by way of illustration and not limitation. It is to be noted that rotatable structure 2900 may comprise any suitable rotatable structure known in the art. Rotatable structure 2900 and knobs 3070 and 3090 typically rotate about a central axis 3300 of tool 3022. As shown (especially in FIGS. 3A-B), housing 3342, spool 3046, and tissue anchor are disposed along axis 3300 of tool 3022.

Adjusting mechanism 40 functions to adjust a dimension of the artificial chordae tendineae, i.e., portions 60A and 60B of longitudinal member 60. Such techniques for artificial chordal adjustment may be implemented using any one of the techniques described in US 2010/0161042 to Maisano et al., which issued as U.S. Pat. No. 8,808,368, and which is incorporated herein by reference. It is to be noted that any number of longitudinal members 60 may be coupled to adjusting mechanism 40.

FIG. 2 shows delivery tool 3022 in its assembled state. System 3000 typically comprises portions 60A and 60B of flexible, longitudinal member 60 which function as the repair chords that are ultimately implanted in the heart of the patient. A portion of longitudinal member 60 that is between portions 60A and 60B of the longitudinal member is coupled by being looped through one or more holes in the spool that is housed within spool housing 3342. Typically, each one of the respective free ends of portions 60A and 60B of longitudinal member 60 is coupled to a tissue-coupling element (e.g., a suture needle 64). For some applications, a portion of shaft 22 is surrounded by a needle holder 70 which is shaped so as to define an engaging component 3030. Component 3030 is typically shaped to define generally planar blades 3032. For some applications, each blade 3032 has at least one respective slit 3160 and 3162. Each slit 3160 and 3162 may house a respective needle 64.

Spool housing 3342 is shaped so as to define respective conduits 3320 and 3322 through which portions 60A and 60B of longitudinal member 60 enter housing 3342 and pass toward the spool disposed within housing 3342. Each portion 60A and 60B of longitudinal member 60 extends from the spool disposed within housing 3342, through a respective secondary lumen 192 of multilumen shaft 22 (as shown in the transverse cross-section of shaft 22) toward needle holder 70. During delivery of spool assembly 240 to the implantation site in the ventricle of the patient, needles 64 are disposed within slits 3160 and 3162 of needle holder 70 so as to facilitate atraumatic delivery of spool assembly 240 to the implantation site. During the coupling of portions 60A and 60B of longitudinal member 60 in the heart of the patient, needles 64 are extracted from within respective slits 3160 and 3162 and portions 60A and 60B of longitudinal member 60 are sutured to cardiac tissue (e.g., a single leaflet of an atrioventricular valve, respective first and second leaflets of the atrioventricular valve, or to a portion of the ventricle wall) that faces and surrounds the ventricular lumen of the heart.

Typically, longitudinal member 60 comprises a flexible and/or superelastic material, e.g., ePTFE, nitinol, PTFE, polyester, stainless steel, or cobalt chrome. In some applications, longitudinal member 60 is coated with polytetrafluoroethylene (PTFE) or with PTFE. In other applications, longitudinal member 60 comprises at least one wire/suture portion and at least one portion that comprises an elongate tensioning coil. For example, portions 60A and 60B of longitudinal member 60 may comprise an elongate coil between two wire/suture portions.

For some applications, following the initial procedure of implantation and adjustment of the artificial chordae tendineae, the respective lengths of portions 60A and 60B of longitudinal member 60 may be adjusted (either shortened or lengthened) from a site outside the patient's body (i.e., immediately following the procedure or during a subsequent procedure). For example, the length may be adjusted by applying RF or ultrasound energy to the members.

For some applications, shaft 22 defines longitudinal slits 122 that run parallel to longitudinal axis 3300 of tool 3022. Once spool assembly 240 is implanted in cardiac tissue (as described hereinbelow), each needle 64 is decoupled from respective slits 3160 and 3162 of needle holder 70 and portions 60A and 60B of longitudinal member are pulled from within lumens 192, via slits 122, and away from longitudinal axis 3300 of tool 3022 in order to release portions 60A and 60B from within shaft 22.

For some applications, one or more guide wires (not shown for clarity of illustration) are (1) coupled at respective first ends thereof to spool housing 3342, (2) extend through respective secondary lumens 194 of multilumen shaft 22, and (3) are coupled at respective second ends thereof to handle portion 3026. Technique for use the guidewires may be practiced in combination with techniques described in above-mentioned US 2010/0161042 to Maisano et al. In such an application, following implantation and adjustment of the repair chords, as described hereinbelow, the guide wires may be cut and pulled away from housing 3342. For other applications, the guide wires are reversibly coupled to housing 3342 by being looped through a portion of the housing. In these applications, following implantation and adjustment of the repair chords, as described hereinbelow, the guide wires may be pulled away from housing 3342. For yet other applications, the guide wires remain disposed within the body of the patient and are accessible at a later stage by an access-port system.

Reference is now made to FIGS. 3A-B, which are schematic cross-sectional illustrations of tool 3022 coupled to adjusting mechanism 40 comprising rotatable structure 2900 (e.g., spool 3046), in accordance with some applications of the present invention. Adjusting mechanism 40 is shown as comprising housing 3342 which defines a recessed portion 142. FIG. 3A shows spool 3046 prior to rotation thereof. As shown in the enlarged image, a portion of longitudinal member 60 is wound a few times (e.g., 3 times, as shown) around the cylindrical body portion of spool 3046. Prior to rotation of spool 3046, portions 60A and 60B of longitudinal member 60 are in a slackened state and longitudinal member 60 is wrapped, or wound, a few times (e.g., 3 times, as shown) around the cylindrical portion of spool 3046, as shown in FIG. 3A.

FIG. 3B shows spool 3046 following rotation thereof. As described hereinabove, adjusting mechanism holder 3029 has a distal end that is reversibly coupled to adjusting mechanism 40, such as to a proximal portion of a housing 3342 surrounding the rotatable structure of adjusting mechanism 40. Holder 3029 is shaped to define a lumen for slidable passage therethrough of a manipulator 3040 which comprises a distal screwdriver head 3042. Screwdriver head 3042 is coupled to rotatable structure 2900 and facilitates rotation of rotatable structure 2900 responsively to the rotation of manipulator 3040. Manipulator 3040 is coupled at a proximal end thereof to a distal end of torque-delivering tool 26 which delivers torque to manipulator 3040 and effects rotation of screwdriver head 3042. As is described herein, a proximal end of torque-delivering tool 26 is coupled to the rotating mechanism at proximal handle portion 3026.

Adjusting mechanism holder 3029 comprises distal graspers 3330 which reversibly couple holder 3029 to adjusting mechanism 40 by grasping a proximal male projection 3346 of spool 3046. Graspers 3330 have a tendency to compress toward one another, and thus are reversibly clamped around proximal projection 3346 of spool 3046.

As shown in the enlarged image, longitudinal member 60 is further wound around spool 3046 a few more times (e.g., an additional 4 times, as shown) around the cylindrical body portion of spool 3046. The rotation of spool 3046 pulls taut portions 60A and 60B of longitudinal member 60.

Rotation of spool 3046 in a first direction winds the longitudinal member 60 around spool 3046, while rotation of spool 3046 in a second direction opposite the first direction, unwinds the portion of longitudinal member 60 from around spool 3046.

Spool 3046 defines an upper surface 150, a lower surface 152 and a cylindrical body portion disposed vertically between surfaces 150 and 152. Spool 3046 is shaped to provide a driving interface, e.g., a channel, which extends from a first opening provided by upper surface 150 to a second opening provided by lower surface 152. A proximal portion of the driving interface is shaped to define a threaded portion 2046 which may or may not be tapered. The cylindrical body portion of spool 3046 is shaped to define one or more holes which function as respective coupling sites for coupling (e.g., looping through the one or more holes, or welding to spool 3046 in the vicinity of the one or more holes) of any number of longitudinal members 60 to spool 3046.

Lower surface 152 of spool 3046 is shaped to define one or more (e.g., a plurality, as shown) recesses 154 which define structural barrier portions of lower surface 152. It is to be noted that any suitable number of recesses 154 may be provided, e.g., between 1 and 10 recesses, (e.g., circumferentially with respect to lower surface 152 of spool 3046).

Reference is still made to FIGS. 3A-B. For some applications, adjusting mechanism 40 comprises a locking mechanism 45, which is disposed in communication with lower surface 152 of spool 3046 and disposed in communication with at least in part to a lower surface of spool housing 3342. Locking mechanism 45 comprises a mechanical element which has a pushed state (FIG. 3A) and a resting state (FIG. 3B). Typically, a cap 44 maintains locking mechanism 45 in place with respect to lower surface 152 of spool 3046 and lower surface of spool housing 3342. For some applications, locking mechanism 45 is coupled, e.g., welded, to the lower surface of housing 3342. Typically, locking mechanism 45 defines slits. It is to be noted that the surface of locking mechanism 45 may also be curved, and not planar. Locking mechanism 45 is shaped to provide a protrusion 156 (or a coupling) which projects out of a plane defined by the planar surface of the mechanical element of locking mechanism 45. The slits of mechanism 45 define a depressible portion 128 that is disposed in communication with and extends toward protrusion 156. Depressible portion 128 is moveable in response to a force applied thereto typically by an elongate locking mechanism release rod 3060 which slides through a lumen of torque-delivering tool 26.

It is to be noted that the planar, mechanical element of locking mechanism 45 is shown by way of illustration and not limitation and that any suitable mechanical element having or lacking a planar surface but shaped to define at least one protrusion may be used together with locking mechanism 45.

For some applications, cap 44 is shaped to define a planar surface and an annular wall having an upper surface thereof. The upper surface of the annular wall is coupled to, e.g., welded to, a lower surface provided by spool housing 3342. The annular wall of cap 44 is shaped to define a recessed portion 144 of cap 44 that is in alignment with recessed portion 142 of spool housing 3342.

Figure 4:
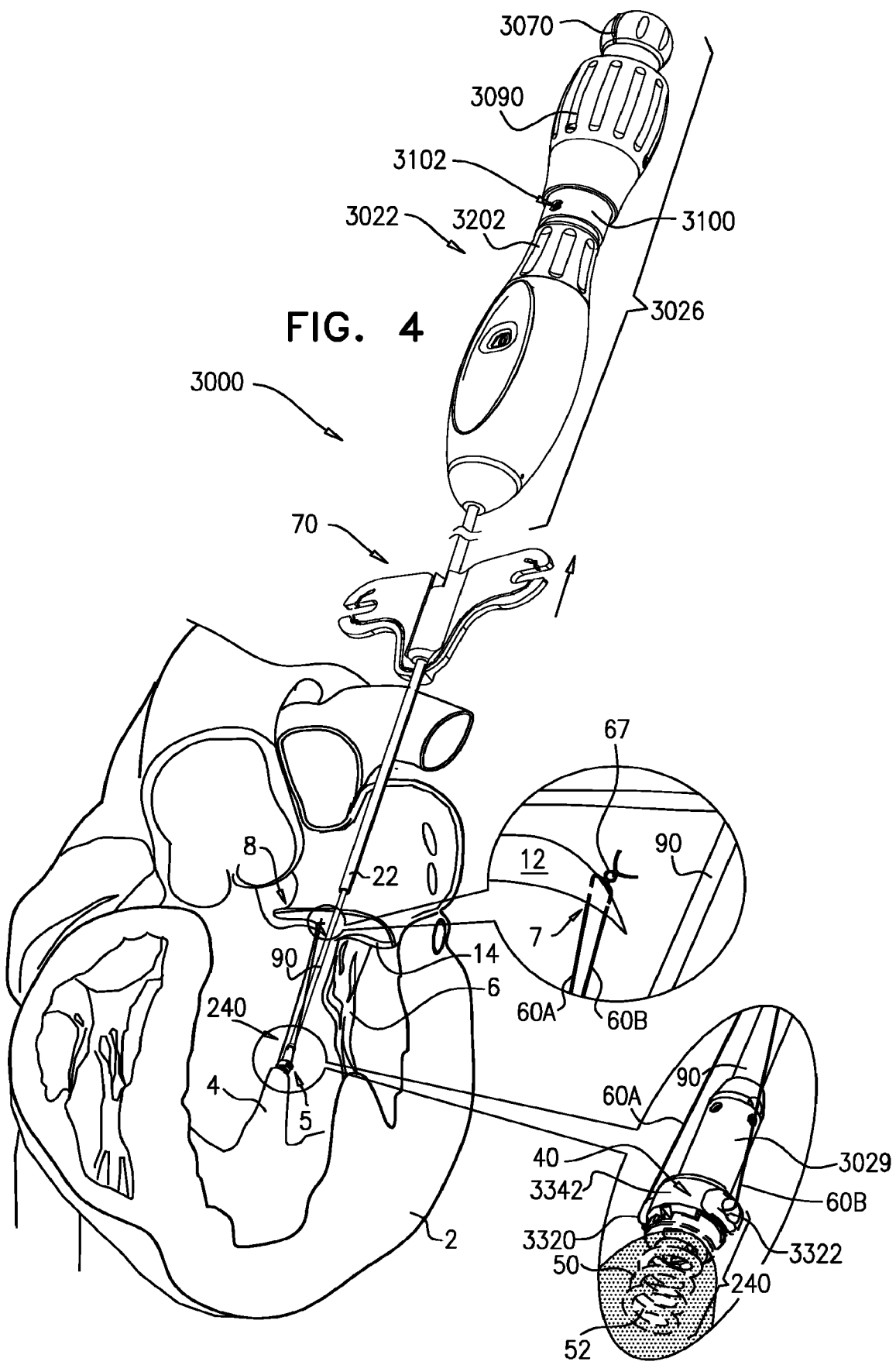
FIG. 4 is a schematic illustration of the delivery tool of FIG. 1 implanting the adjusting mechanism in a heart of a patient, in accordance with some applications of the present invention.

Reference is now made to FIG. 4, which is a schematic illustration of tool 3022 facilitating implantation of anchor 50 of spool assembly 240 in cardiac tissue and adjustment of longitudinal member 60 functioning as artificial chords, in accordance with some applications of the present invention. Following implantation of anchor 50, tool 3022 facilitates rotation of the spool of adjusting mechanism 40.

It is to be noted that although adjusting of artificial chords in order to repair mitral valve 8 is shown herein, system 3000 may additionally be used to implant and adjust artificial chords in order to repair a tricuspid valve of the patient.

Spool housing 3342 is typically surrounded by a braided fabric mesh, e.g., a braided polyester mesh, which promotes fibrosis around assembly 240 over time subsequently to the implantation of assembly 240 and the adjustment of longitudinal member 60. Additionally, during the initial implantation of assembly 240, spool housing 3342 may be sutured via the mesh to the cardiac tissue (e.g., during an open-heart procedure).

Reference is now made to FIGS. 1, 3A-B, and 4. Prior to rotating spool 3046, anchor 50 of assembly 240 is implanted at an implantation site at cardiac tissue of the patient, e.g., a papillary muscle 4 (as shown) or a portion of tissue of an inner wall of the ventricle (e.g., a portion of the wall in a vicinity of the apex, a portion of a free wall, or a portion of the wall in a vicinity of the septum). Implantation of spool assembly 240 is facilitated by tool 3022. An incision is made in heart 2, and tissue anchor 50, adjusting mechanism 40, longitudinal member 60, and a distal portion of shaft 22 are advanced between leaflets 12 and 14 of mitral valve 8 and toward papillary muscle 4. Assembly 240 is advanced until pointed tip 52 of anchor 50 abuts papillary muscle 4. A knob 3202 is rotated in a first rotational direction in order to rotate housing 3342 and anchor 50 in a first rotational direction without rotating spool 3046 disposed within assembly 240 (i.e., spool 3046 is not rotated relative to housing 3342 in response to rotation of housing 3342 and anchor 50).

As shown in FIG. 1, knob 3202 is coupled to a structural component 3200 (i.e., a distal portion of knob 3202 is fixed to a proximal portion of component 3200). As knob 3202 is rotated, component 3200 is rotated, which rotates shaft 22 that is coupled at a proximal end thereof to a distal portion of handle portion 3026. Shaft 22, in turn, surrounds and facilitates slidable coupled of an overtube 90, which in turn, surrounds torque-delivering tool 26 (as shown in the enlarged cross-sectional images of FIGS. 3A-B). Overtube 90 is coupled at a distal end thereof to adjusting mechanism holder 3029.

Rotation of knob 3202 rotates shaft 22, and thereby overtube 90 is rotated, which rotates holder 3029 and thereby rotates anchor 50 and housing 3342 of spool assembly 240. During rotation of overtube 90, torque-delivering tool 26 is not rotated within the lumen of overtube 90. Therefore, spool 3046 is not rotated with respect to spool housing 3342 as knob 3202 is rotated in order to rotate anchor 50 and housing 3342 of spool assembly 240. Spool 3046 is not rotated within housing 3342 with respect to tissue anchor 50 or housing 3342 because torque-delivering tool 26 is not rotated relative to tool 3022. (Rotation of spool 3046, with respect to housing 3342, occurs subsequently to rotation of tissue anchor 50 and housing 3342 of assembly 240 and responsively to rotation of torque-delivering tool 26 in order to rotate manipulator 3040 and thereby spool 3046. During such rotation of spool 3046, tissue anchor 50 and housing 3342 are not rotated.) Rotation of knob 3202 screws anchor 50 into cardiac tissue of the patient, and thereby implants spool assembly 240 in the ventricle of heart 2.

During the screwing of anchor 50 into cardiac tissue, spool 3046 is not rotated with respect to housing 3342 so as to prevent manipulation of the tension of flexible longitudinal member 60 at the same time that spool assembly 240 is being implanted in heart 2.

Reference is again made to FIG. 1. For some applications, knob 3202 is coupled to structural component 3200, which is shaped so as to define a helical groove 3260 having a distal end 3262. Groove 3260 provides a track 3263 for advancement of a pin 3064 therealong. Prior to rotation of knob 3202, pin 3064 is disposed at a proximal end portion of groove 3260. As knob 3202 is rotated in a first direction, component 3200 is rotated in the first direction while pin 3064 remains in place. Component 3200 advances with respect to pin 3064 as groove 3260 advances around pin 3064. Concurrently, pin 3064 advances linearly distally with respect to hand-grasping portion 3120 that defines a slit 3067 along which pin 3064 advances distally. Pin 3064 is coupled to lateral projection 3068 of a slidable numerical indicator 3066. Indicator 3066 is configured to remotely indicate the number of rotations of tissue anchor 50 during the screwing of assembly 240 into tissue of the patient.

As pin 3064 distally advances linearly along slit 3067, indicator 3066 advances linearly along a track provided by an undersurface of a cover 3182 that is coupled to hand-grasping portion 3120 and covers slit 3067. Cover 3182 remains stationary as indicator 3066 advances linearly with respect to cover 3182. Cover 3182 is shaped so as to define a window 3180 which displays a number of the series of numbers of indicator 3066 as it advances linearly with respect to cover 3182. This number indicates the number of rotations of assembly 240. As knob 3202 is rotated, a distal end 3262 of groove 3260 approaches pin 3064, and indicator 3066 indicates a higher number in the series of numbers. Once distal end 3262 of groove 3260 contacts pin 3064, rotation of knob 3202, and thereby rotation of spool assembly 240, is restricted. That is, tool 3022 restricts implantation of anchor 50 beyond a predetermined amount of rotations (e.g., 4 rotations as indicated by indicator 3066) in order to prevent over-screwing of assembly 240 into tissue.

Rotation of knob 3202 in a second direction, opposite the first, causes component 3200 to rotate in the second direction. Rotation of component 3200 in the second direction rotates overtube 90 and holder 3029 in the second direction, and responsively, tissue anchor 50 of spool assembly 240 is unscrewed from the tissue. Additionally, pin 3064 is advanced proximally as groove 3260 slides around pin 3064. Pin 3064 thus causes indicator 3066 to indicate a lower number in the series of numbers.

Reference is again made to FIG. 4. Following implantation of assembly 240, portions 60A and 60B of longitudinal member 60 are coupled (e.g., sutured, knotted, or otherwise fastened) to leaflet 12. As shown, portions 60A and 60 may be knotted to leaflet 12 via knot 67. The adjusting of adjusting mechanism 40 functions to generally return leaflet 12 to its physiological state and provide artificial chordae tendineae. For some applications, first portion 60A may be coupled to leaflet 12 while second portion 60B may be coupled to leaflet 14. In such applications, the adjusting of adjusting mechanism 40 may function to draw together leaflets 12 and 14.

Prior to coupling of portions 60A and 60B to leaflet 12, as shown (or to both leaflets 12 and 14), shaft 22 is slid proximally along overtube 90 such that a distal end thereof is disposed proximally to mitral valve 8 in the atrium of heart 2 (as shown in FIG. 4).

Reference is now made to FIGS. 1, 3A, and 4. As shown in FIG. 3A, a distal end of shaft 22 is coupled to a shaft-coupler 3027 (and fastened thereto by a fastener 3025). Shaft-coupler 3027 slides along a slit 3024 of a portion of handle portion 3026 (shown in FIG. 1) which defines a lumen 3023 for passage therethrough of a proximal portion of shaft 22. The operating physician pulls proximally on holder 70 that surrounds a portion of shaft 22. As holder 70 is pulled, shaft 22 is slid proximally such that a proximal portion thereof is slid into lumen 3023 of handle portion 3026. Alternatively or additionally, the physician may pull proximally on a portion of shaft 22 by grabbing a portion of shaft 22. The sliding of shaft 22 proximally exposes a proximal portion of overtube 90 (shown in FIG. 4). Sliding of shaft 22 thus reduces the diameter of the portion of tool 3022 that is disposed between leaflets 12 and 14, and thus, reduces interference of tool 3022 on the beating of valve 8 as portions 60A and 60B of longitudinal member 60 are adjusted.

Reference is now made to FIGS. 2 and 4. Following the sliding of shaft 22, needles 64 are removed from slits 3160 and 3162 of holder 70 and pulled so that the pulling of respective needles 64 pulls portions 60A and 60B of longitudinal member 60 from within lumens 192 of shaft 22 (i.e., via slits 122 of shaft 22 that extend along shaft 22 toward holder 70). Needles 64 are used to suture portions 60A and 60B to leaflet 12, and then portions 60A and 60B are clipped proximally to knot 67 and excess portions of longitudinal members 60 (as shown in FIG. 4), and needles 64 are removed from heart 2. The incision in heart 2 is then closed around shaft 22, e.g., using a purse-string stitch, and the patient is removed from the cardiopulmonary bypass pump so that heart 2 resumes beating during the subsequent adjustment of portions 60A and 60B by rotation of spool 3046 of adjusting mechanism 40.

Reference is again made to FIGS. 3A-B. FIG. 3A shows adjusting mechanism 40 in an unlocked configuration in which protrusion 156 of locking mechanism 45 is disposed within recessed portion 144 of cap 44. FIG. 3B shows adjusting mechanism 40 in a locked state thereof due to the positioning of protrusion 156 within a recess 154 of spool 3046.

Manipulator 3040, comprising screwdriver head 3042, is coupled to the distal end of torque-delivering tool 26. A proximal end of torque-delivering tool 26 is coupled to a rotating mechanism in proximal handle portion 3026 of tool 3022. The rotating mechanism comprises a torque-delivering-tool rotator 3080 which is rotated at different times during a surgical procedure by knobs 3070 and 3090. Torque-delivering-tool rotator 3080 comprises a cylindrical structure which is shaped to define a lumen 3077 (shown in FIG. 3B) and an opening at a proximal end thereof. Lumen 3077 of rotator 3080 provides a slidable coupling arrangement for an elongate structural component 3071 that is coupled to knob 3070. One or more pins 3084 (e.g., 1 pin, as shown) are coupled to a distal end of component 3071. Rotator 3080 is shaped to define one or more slits 3082 (e.g., 1 slit, as shown) through each projects a first portion of a respective pin 3084 in order to couple component 3071 to rotator 3080. Additionally, knob 3090 is shaped so as to define one or more slits 3085 (e.g., 1 slit, as shown) through each projects a second portion of a respective pin 3084 during a pushed state of knob 3070, as shown in FIG. 3A. Since the first and second portions of pin 3084 are disposed within slits 3082 and 3085, respectively, pin 3084 mechanically couples knob 3090 to rotator 3080 during the pushed state of knob 3070, as shown in FIG. 3A.

A distal portion of rotator 3080 is coupled, e.g., welded, to a proximal portion of torque-delivering-tool 26 such that rotation of rotator 3080 (e.g., by knob 3090) rotates torque-delivering tool 26, and responsively, manipulator 3040 and screwdriver head 3042 are rotated, and, in turn, spool 3046 is rotated. Thus, rotation of knob 3090 rotates spool 3046. During rotation of knob 3090, torque-delivering tool 26 is rotated relative to overtube 90 and shaft 22 (that is, overtube 90 and shaft 22 are not rotated responsively to the rotation of tool 26). In such a manner, spool 3046 is rotated within housing 3342, while housing 3342 and anchor 50 are not rotated.

It is to be noted that implantation of tissue anchor 50 and the subsequent rotation of spool 3046 occur during a single advancement of tool 3022 within heart 2. Additionally, implantation of tissue anchor 50 and the subsequent rotation of spool 3046 typically occur along a single axis of rotation, i.e., axis 3300 of tool 3022. That is, tool 3022 remains along and is not moved away from (e.g., left, right, back, or forth) the axis of rotation during the rotation of spool 3046 following the screwing to tissue anchor 50 in order to implant tissue anchor 50. Furthermore, implantation of tissue anchor 50 and the subsequent rotation of spool 3046 typically occur without extracting at least the distal end of tool 3022 from within heart 2 of the patient. That is, implantation of tissue anchor 50 and the subsequent rotation of spool 3046 typically occur during a single advancement of tool 3022.

Reference is now made to FIGS. 1 and 3A-B. Knob 3070 is shaped to define a groove 3073 (as shown in FIG. 1). A flexible, semi-rigid release clip 3072 is coupled to knob 3070 and is disposed within groove 3073. Clip 3072 is shaped to define male couplings 3074 at respective distal ends of clip 3072. Couplings 3074 function to lock knob 3070 with respect to handle portion 3026 during a pushed state of knob 3070 (FIG. 3A). FIG. 3A shows knob 3070 in a pushed state in which (1) the proximal portion of component 3071 is disposed within the lumen of rotator 3080, (2) pin 3084 is disposed at a distal end of slit 3082 of rotator 3080 and at a distal end of slit 3085 of knob 3090, and (3) male couplings 3074 are disposed, and locked in place within respective female couplings 3081 of rotator 3080. The coupling of male and female couplings 3074 and 3081, respectively, enable knob 3070 to remain in a locked position. FIG. 3B shows knob 3070 following the proximal release of knob 3070 along central axis 3300 of tool 3022, in which a proximal portion of component 3071 is exposed proximal to lumen 3077 of rotator 3080, couplings 3074 are disposed proximally to the opening of rotator 3080, and pin 3084 is disposed in a proximal position within slit 3082 of rotator 3080 (and no longer within slit 3085 of knob 3090).

The pushed state of knob 3070 compresses and applies load to a tension spring 3078 that is disposed within knob 3070 and component 3071. As shown in FIG. 3A, a proximal end of elongate locking mechanism release rod 3060, is coupled to release rod holder 3061, which is coupled to component 3071. Pushing distally of knob 3070 (and thereby component 3071) advances holder 3061 distally, which, in turn, pushes distally release rod 3060. Release rod 3060 extends through tool 3022 from handle portion 3026 and toward distal portion 3028 of tool 3022, and is surrounded, for the most part, by torque-delivering tool 26. During a resting state of tool 3022 (i.e., when knob 3070 is not pushed distally, as shown in FIG. 3B), a distal end 3062 of rod 3060 is disposed within torque-delivering tool 26 proximally to and does not engage adjusting mechanism 40 (as shown in the enlarged image of FIG. 3B).

It is to be noted that in order to release locking mechanism 45 from spool 3046, protrusion 156 should be pushed distally by rod 3060 between 0.3 and 1.0 mm, e.g., 0.4 mm. When tool 3022 is decoupled from adjusting mechanism 40 and knob 3070 is disposed in a pushed state, the distal end portion of rod 3060 extends approximately 5 mm beyond the distal end of tool 3022. When adjusting mechanism 40 is coupled to tool 3022, and rod 3060 is pushed distally (as shown in FIG. 3A), distal end 3062 of rod 3060 contacts and is impeded by depressible portion 128 of locking mechanism 45. Depressible portion 128 is capable of being depressed by an angle of up to 20 degrees, e.g., 7 degrees (i.e., cap 44 restricts depressing of portion 128 beyond a certain angle). When distal end 3062 of rod 3060 contacts portion 128, portion 128 restricts rod 3060 from extending further than 1 mm from second opening 182 of spool 3046. In order to compensate for the restricting of the extension of rod 3060 beyond a predetermined amount, spring 3078 contracts in order to slightly pull back rod 3060. Spring 3078 thus enables tool 3022 to be generally exacting in pushing protrusion 156 distally by 0.3-0.5, e.g., 0.4 mm.

Reference is again made to FIGS. 1 and 3A-B. In response to the pushing of knob distally, release rod 3060 slides distally within a lumen of torque-delivering tool 26 such that a distal portion of rod 3060 slides through lumen 3044 of manipulator 3040 (lumen 3044 is shown in the enlarged image of FIG. 3A), through screwdriver head 3042, and then through a channel of spool 3046. A distal end 3062 of rod 3060 advances through the channel of spool 3046, beyond the opening provided by lower surface 152 of spool 3046, and presses distally on depressible portion 128 of locking mechanism 45. Since depressible portion 128 is connected to protrusion 156, pushing distally on depressible portion 128 pushes protrusion 156 distally from within recess 154 of spool 3046, thereby freeing spool 3046 from locking mechanism 45 (as shown in FIG. 3A). As protrusion 156 is pushed, it advances distally within recessed portion 144 of cap 44 and away from recessed portion 142 of housing 3342.

It is to be noted that any elongate structure, e.g., a pull-wire, a rod, a thread, rope, or a suture, may be passed through the lumen of torque-delivering tool 26 independently of and/or in addition to rod 3060. It is to be noted that any elongate structure, e.g., a pull-wire, a rod, a thread, rope, or a suture, may be passed through the lumen of shaft 22 independently of and/or in addition to tool 26.

Typically, tool 26 comprises a flexible material (e.g., a plastic or a plurality of strands of flexible metal such as stainless steel 304 that are bundled together). Once protrusion 156 is displaced from within recess 154 of spool 3046, and spool 3046 is released from locking mechanism 45, the physician rotates knob 3090 in a first direction thereof in order to rotate spool 3046, as described hereinabove. Tool 3022 is free to rotate spool 3046 in either clockwise or counterclockwise direction, as long as protrusion 156 of locking mechanism 45 is decoupled from spool 3046. The physician is able to freely rotate knob 3090 (and thereby spool 3046) without any obstruction from locking mechanism 45 because locking mechanism 45 is kept in an unlocked state (i.e., protrusion 156 remains outside of the recesses 154 of spool 3046) due to the pushed state of knob 3070 of tool 3022. During this pushed state, knob 3070 is maintained in a pushed state as male couplings 3074 are coupled to female couplings 3081, and rod 3060 is maintained in a state in which distal end 3062 is disposed distally to the opening provided by lower surface 152 of spool 3046 and pushes on depressible portion 128 of locking mechanism 45, as shown in the enlarged image of FIG. 3A.

Reference is again made to FIGS. 1 and 3A-B. As described hereinabove, the pushed state of knob 3070 (as shown in FIG. 3A) releases locking mechanism 45 from spool 3046. Additionally, the pushed state of knob 3070 engages the rotating mechanism of tool 3022 (which comprises rotator 3080) with knob 3090. In a resting state of tool 3022, as shown in FIG. 3B, knob 3070 is disposed in its proximal-most position and pin 3084 is disposed within slit 3082 of rotator 3080 proximally to knob 3090. As shown in FIGS. 3A-B, knob 3090 is shaped to define slit 3085 along a portions of the inner wall thereof that defines a lumen in which a distal portion of rotator 3080 is disposed.

Slit 3082 of rotator 3080 enables slidable advancement of pin 3084 during the distal sliding of component 3071 within lumen 3077 of rotator 3080 responsively to pushing and pulling of knob 3070. During the resting state of tool 3022, as shown in FIG. 3B, knob 3070 is not pushed, and a proximal portion of component 3071 is exposed from within lumen 3077 of rotator 3080. Pin 3084 is disposed proximally to knob 3090, as shown in the enlarged image of FIG. 3B. During the pushed state of knob 3070, pin 3084 is disposed at a distal end of slit 3082 of rotator 3080 and at a distal end of slit 3085 of knob 3090.

Pin 3084 passes through slit 3085 of knob 3090. In an un-pushed state of knob 3070, as shown in FIG. 3B, pin 3084 is disposed proximally to the proximal end of slit 3085. In the pushed state of knob 3070, as shown in FIG. 3A, pin 3084 is disposed within respective slit 3085 of knob 3090. It is to be further noted that tool 3022 comprises one pin 3084 by way of illustration and not limitation, and that any suitable number of pins 3084 may be coupled to tool 3022 in accordance with the number of slits 3085. For example, if tool 3022 has 4 slits 3085, then tool 3022 may comprise between 1 and 4 pins 3084.

In the pushed state of knob 3070, since knob 3090 is coupled to rotator 3080, (and spool 3046 is now freed from locking mechanism due to the pushed state of knob 3070, as described hereinabove) rotation of knob 3090 in a first direction thereof (i.e., counterclockwise), rotates spool 3046 in the first direction and winds longitudinal member 60 around spool 3046. Once freed from locking mechanism 45, manipulator 3040 of tool 3022 can rotate spool 3046 bidirectionally. Rotation of knob 3090 in a second direction (i.e., clockwise) opposite the first direction rotates spool 3046 in the opposite direction and unwinds longitudinal member 60 from around spool 3046.

Reference is yet again made to FIGS. 1 and 3A-B. Tool 3022 is shaped to define a helical groove 3092 that is shaped to define an indented track 3095. As described hereinabove, knob 3090 is coupled to the rotation mechanism of tool 3022, because pin 3084 couples rotator 3080 to knob 2090 in the pushed state of knob 3070 when pin 3084 is disposed within slit 3085 of knob 3090 (as shown in FIG. 3A). Knob 3090 is coupled at a distal end thereof to a tiered, or terraced, screw 3094, as shown in FIGS. 3A-B. A narrow end portion of screw 3094 is disposed within a portion of track 3095 and is helically advanceable distally and proximally responsively to rotation of knob 3090. FIG. 3A shows tool 3022 prior to rotation of knob 3090 in the first direction, in which screw 3094 is disposed in a proximal portion of track 3095 of helical groove 3092.

Knob 3090 is coupled at a distal end 3091 thereof to a sliding indicator 3100 which is shaped to define a window 3102 (shown in FIG. 1). Rotation of knob 3090 in the first direction helically advances screw 3094 distally. This motion pushes linearly and distally sliding indicator 3100. Sliding indicator 3100 slides distally and proximally along a cylindrical body component 3106 responsively to rotation of knob 3090 in first and second directions, respectively. Component 3106 displays a series of numbers 3104. As indicator 3100 slides along component 3106, window 3102 displays one or a portion of one or more of numbers 3104, in order to indicate the number of rotations of spool 3046. Numbers 3104 provide, by way of illustration and not limitation, numbers −3 to 4. Typically, in a resting state of tool 3022, indicator 3100 is disposed at a middle section of groove 3092 in which window 3102 displays the number 0 in the series of numbers 3104.

In the resting state (i.e., the 0-state of spool 3046) of contracting mechanism 40, longitudinal member 60 is wound around spool 3046 three times, as shown in the enlarged cross-sectional image of FIG. 3A. This winding provides excess slack to member 60 (in case portions 60A and 60B are coupled too tightly to leaflet 12). If the physician wishes to provide slack to member 60, the physician unwinds a portion of member 60 from around spool 3046. In order to accomplish such unwinding, the physician rotates knob 3090 in the second direction thereof, i.e., opposite the first direction. During the rotation of knob 3090 in the second direction, screw 3094 advances helically proximally along groove 3092 and indicator 3100 displays the negative numbers. In the 0-state of spool 3046 and in the unwound state of member 60, portions 60A and 60B are slackened, as shown in FIG. 3A. When indicator 3100 is slid distally and window 3102 reaches −3, member 60 is fully unwound from spool 3046. Since member 60 is looped through spool 3046, in the −3 state of spool 3046 when member 60 is not wound around spool 3046, the physician can pull the free ends of portions 60A and 60B so as to adjust or make even portions 60A and 60B that extend from spool 3046.

When the physician wishes to tighten member 60 (i.e., to tighten the artificial chord), the physician winds a portion of member 60 around spool 3046. In order to accomplish such winding, the physician rotates knob 3090 in the first direction thereof, i.e., opposite the second direction. During such rotation of knob 3090 in the first direction, screw 3094 advances distally helically along groove 3092 and indicator 3100 advances toward the positive numbers of numbers 3104. As shown in the enlarged cross-sectional image of FIG. 3B, member 60 is wound around spool a total of 7 times, i.e., 4 winds of member 60 around spool in addition to the 3 winds of member 60 at the 0-state of spool 3046. As shown in FIG. 3B and in FIG. 4, as spool 3046 is wound in the first direction and member 60 is wound sufficiently around spool 3046, portions 60A and 60B of member 60 are pulled taut.

Reference is now made to FIGS. 1 and 3A. The proximal annular portion of sliding indicator 3100 is shaped so as to define a plurality of teeth 3093. Knob 3090 is coupled to and houses at a distal end 3091 thereof a plunger 3097 (shown in FIG. 1). As knob 3090 is rotated, plunger 3097 rotates along teeth 3093 of the proximal annular portion of indicator 3100 and thereby provides an audible indication of the number of times the physician rotates knob 3090.

Reference is now made to FIG. 3B, which is a schematic illustration of tool 3022 following rotation of knob 3090, in accordance with some applications of the present invention. As described hereinabove, knob 3090 is rotated in the first direction in order to helically advance screw 3094 distally along track 3095 of helical groove 3092.

Reference is now made to FIGS. 1 and 3A-B. Helical groove 3092 is shaped to define a certain number of rotations (e.g., 7, as shown by way of illustration and not limitation in the figures). A distal end 3096 of groove 3092 (shown in FIG. 1) provides a termination point at which screw 3094 is restricted from being advanced further distally, and rotation of knob 3090 in the first direction is thereby restricted. Restriction of rotation of knob 3090 beyond a predetermined point restricts rotation of spool 3046 beyond a predetermined amount of rotations, e.g., 4 additional rotations from the 0-state of spool 3046), as shown by way of illustration and not limitation. It is to be noted that because knob 3070 is also coupled to rotator 3080, rotation of knob 3070 also facilitates rotation of spool 3046. However, rotation of spool 3046 via knob 3070 does not rotate screw 3094 along groove 3092, and thereby rotation of spool 3046 is not restricted nor indicated by indicator 3100. Alternatively, rotation of spool 3046 using knob 3090 is (1) eventually restricted by the distal end of groove 3092, and (2) indicated by sliding indicator 3100. Therefore, rotation of spool 3046 is typically but not necessarily performed responsively to rotation of knob 3090.

As knob 3090 is rotated, it advances together with indicator 3100 distally along body component 3106 of tool 3022.

Following rotation of spool 3046 (typically but not necessarily responsively to the rotation of knob 3090), screw 3094 is disposed at a distal end of groove 3092 (e.g., near or at distal end 3096 of groove 3092), and indicator 3100 is disposed at a distal position in which window 3102 approaches the distal-most number (i.e., number 4) in the series of numbers 3104, indicating (1) that spool 3046 has been rotated about 4 times from its 0-state, (2) that longitudinal member 60 has been wound around spool 3046 about an additional 4 times from its 0-state, and/or (3) the level of contraction of the portions 60A and 60B of longitudinal member 60 that is coupled to adjusting mechanism 40.

Reference is now made to FIGS. 3A-B. Rotation of knob 3090 in the first direction, and thereby of spool 3046 in the first direction, winds a longitudinal member 60 around spool 3046. As described herein, rotation of knob 3090 in the second direction opposite the first direction advances screw 3094 proximally along groove 3092, and rotates spool 3046 in the second direction thereof. Winding of spool 3046 in the second direction unwinds longitudinal member 60 from around spool 3046 in accordance with the number of rotations of knob 3090 in the second direction.

Following rotation of spool 3046 and adjustment of the length of the artificial chordae, tool 3022 is decoupled from adjusting mechanism 40. FIG. 3A shows knob 3070 in a pushed state in which male couplings 3074 of clip 3072 are locked in place within female couplings 3081 of rotator 3080. Additionally, in the pushed state of knob 3070, spring 3078 is compressed. In order to lock spool 3046 in place following rotation of spool 3046 following a desired level of rotation of spool 3046 (e.g., in response to a desired level of contraction of portions 60A and 60B of longitudinal member 60), the operating physician pushes inwardly the lateral portions of clip 3072 coupled to knob 3070 in order to release knob 3070 from its pushed state. Male couplings 3074 of clip 3072 are pushed inwardly within groove 3073 as the lateral portions of clip 3072 are pushed toward central axis 3300 of tool 3022. This pushing of male couplings 3074 inwardly frees male couplings 3074 from within respective female couplings 3081 (shown in FIG. 3B). Responsively, spring 3078 expands from its compressed state, and knob 3070 is pushed proximally in response to the force of spring 3078.

As spring 3078 expands, it pulls proximally release rod holder 3061 and release rod 3060 coupled thereto. As rod 3060 is pulled proximally, it slides proximally within the lumen of torque-delivering tool 26 such that distal end 3062 of rod 3060 no longer pushes distally depressible portion 128 of locking mechanism 45 (as shown in the enlarged cross-sectional image of FIG. 3B). Responsively to the retracting proximally of rod 3060, depressible portion 128 returns to its resting state (i.e., not its pushed state, as shown in FIG. 3A) and thereby returns protrusion 156 into one of the recesses 154 of spool 3046 and back into recessed portion 142 of housing 3342. Once protrusion 156 is placed in recess 154 of spool 3046, spool 3046 is locked in place by locking mechanism 45 and is restricted from being rotated by tool 3022.

As knob 3070 is released, knob 3070 is responsively pushed proximally from the proximal end of knob 3090 by expansion of spring 3078. As knob 3070 advances proximally, component 3071 that is coupled to knob 3070 slides proximally within lumen 3077 of rotator 3080 and pin 3084 slides proximally along slit 3082 of rotator 3080 and along slit 3085 of knob 3090 (as shown in FIG. 3B).

The physician then rotates knob 3070 in order to unscrew screwdriver head 3042 from threaded portion 2046 of spool 3046. Rotation of knob 3070 rotates torque-delivering tool 26, as described hereinabove, which rotates manipulator 3040. Unscrewing screwdriver head 3042 from spool 3046 decouples manipulator 3040 from spool 3046. It is to be noted that spool 3046 is not rotated during the rotation of knob 3070 in order to decouple manipulator 3040 from spool 3046 because spool 3046 is locked in place by locking mechanism 45. The physician then pulls proximally tool 3022 in order to release housing 3342 of adjusting mechanism 40 from graspers 3330 of adjusting mechanism holder 3029, and thereby decouple tool 3022 from adjusting mechanism 40.

Once tool 3022 is disengaged from adjusting mechanism 40 following the adjusting of the dimension of the artificial chordae tendineae, and thereby of leaflet(s) 12 or 14 of valve 8, tool 3022 is extracted from the heart. Holder 3029 is shaped so as to define a cone-shaped proximal portion which acts as an obturator to enlarge the opening surrounded by the purse-string stitch. This shape enables ease and atraumatic extracting of distal portion 3028 of tool 3022. Following the extracting of tool 3022, the opening in the heart is closed, e.g., sutured, and the access site to the body of the patient is sutured.

If the physician wishes to recouple tool 3022 to adjusting mechanism 40 following the decoupling of tool 3022 from adjusting mechanism 40, the physician should rotate knob 3070 in order to recouple screwdriver head 3042 with threaded portion 2046 of spool 3046. As the operating physician rotates knob 3070, structural component 3071 rotates and, since component 3071 is coupled to rotator 3080 via pin 3084, rotator 3080 rotates responsively to rotate torque-delivering tool 26 and thereby manipulator 3040.

Delivery tool 3022 is recoupled to mechanism 40 when graspers 3330 of holder 3029 surround projection 3346 of spool 3046, which provides initial coupling of tool 3022 to adjusting mechanism 40. During the initial coupling, manipulator 3040 may be pushed proximally, along central axis 3300 of tool 3022, by the force of contact of adjusting mechanism 40 to tool 3022. Manipulator 3040 is coupled to a distal end of torque-delivering tool 26, which in turn, is coupled at a proximal end thereof to torque-delivering-tool rotator 3080. Torque-delivering tool 26 slides within over-tube 90 which is disposed within a primary lumen 190 of shaft 22 (as shown in the cross-sectional illustration of FIG. 2). Tool 3022 enables such proximal pushing of manipulator 3040 by providing a tensile spring 3087 (shown in FIGS. 1 and 3A-B) around a proximal portion of rotator 3080 that is coupled to torque-delivering tool 26. As screwdriver head 3042 contacts adjusting mechanism 40, adjusting mechanism 40 responsively pushes and slides proximally (1) screwdriver head 3042 (2) manipulator 3040, (3) torque-delivering tool 26, and (4) rotator 3080. Responsively to the pushing of torque-delivering-tool 26, spring 3087 is compressed to enable such proximal sliding of (1) screwdriver head 3042 (2) manipulator 3040, (3) torque-delivering tool 26, and (4) rotator 3080.

Following the initial recoupling of adjusting mechanism 40 to tool 3022, tool 3022 is then more firmly coupled to adjusting mechanism 40 by screwing screwdriver head 3042 into threaded portion 2046 (shown in FIGS. 3A-B) of spool 3046 of adjusting mechanism 40. By the screwing, screwdriver head 3042 is advanced distally toward adjusting mechanism 40. This screwing of head 3042 is accomplished when the physician rotates knob 3070 in the first direction (i.e., counterclockwise), which, in conjunction, rotates (1) component 3071, (2) rotator 3080, (3) torque-delivering tool 26, and finally, (4) screwdriver head 3042 of manipulator 3040. Responsively, screwdriver head 3042 screws into threaded portion 2046 of spool 3046, and thereby, adjusting mechanism 40 is firmly coupled to tool 3022. Once tool 3022 is firmly coupled to adjusting mechanism 40, tool 3022 (1) frees spool 3046 from locking mechanism 45, and (2) rotates spool 3046, as described hereinabove.

Reference is now made to FIGS. 1, 2, 3A-B, and 4. It is to be noted that the method and apparatus for using the same delivery tool to both (1) facilitate screwing of the tissue anchor into tissue of the patient (while not facilitating rotation of rotatable structure 2900), and (2) subsequently rotate rotatable structure 2900, may be applied in a percutaneous or transcatheter procedure, mutatis mutandis.

For some applications, techniques described herein are practiced in combination with techniques described in one or more of the references cited in the Background section and Cross-references section of the present patent application.

As appropriate, techniques described herein are practiced in conjunction with methods and apparatus described in one or more of the following patent applications, all of which are assigned to the assignee of the present application and are incorporated herein by reference:

PCT Publication WO 06/097931 to Gross et al., entitled, "Mitral Valve treatment techniques," filed Mar. 15, 2006;

U.S. Provisional Patent Application 60/873,075 to Gross et al., entitled, "Mitral valve closure techniques," filed Dec. 5, 2006;

U.S. Provisional Patent Application 60/902,146 to Gross et al., entitled, "Mitral valve closure techniques," filed Feb. 16, 2007;

U.S. Provisional Patent Application 61/001,013 to Gross et al., entitled, "Segmented ring placement," filed Oct. 29, 2007;

PCT Publication WO 08/068756 to Gross et al., entitled, "Segmented ring placement," filed Dec. 5, 2007;

U.S. patent application Ser. No. 11/950,930 to Gross et al., entitled, "Segmented ring placement," filed Dec. 5, 2007, which published as US 2008/0262609, and which issued as U.S. Pat. No. 8,926,695;

U.S. patent application Ser. No. 12/435,291 to Maisano et al., entitled, "Adjustable repair chords and spool mechanism therefor," filed on May 4, 2009, which published as US 2010/0161041, and which issued as U.S. Pat. No. 8,147,542;

U.S. patent application Ser. No. 12/437,103 to Zipory et al., entitled, "Annuloplasty ring with intra-ring anchoring," filed on May 7, 2009, which published as US 2010/0286767, and which issued as U.S. Pat. No. 8,715,342;

PCT Publication WO 10/004546 to Gross et al., entitled, "Annuloplasty devices and methods of delivery therefor," filed on Jun. 15, 2009;

U.S. patent application Ser. No. 12/548,991 to Maisano et al., entitled, "Implantation of repair chords in the heart," filed on Sep. 21, 2009, which published as US 2010/0161042 and which issued as U.S. Pat. No. 8,808,368;

PCT Publication WO 10/073246 to Cabin et al., entitled, "Adjustable annuloplasty devices and mechanisms therefor," filed Dec. 22, 2009;

U.S. patent application Ser. No. 12/706,868 to Miller et al., entitled, "Actively-engageable movement-restriction mechanism for use with an annuloplasty structure," filed Feb. 17, 2010, which published as US 2010/0211166, and which issued as U.S. Pat. No. 8,353,956;

PCT Patent Application PCT/IL2010/000357 to Maisano et al., entitled, "Implantation of repair chords in the heart," filed May 4, 2010, which published as WO 2010/128502; and/or PCT Patent Application PCT/IL2010/000358 to Zipory et al., entitled, "Deployment techniques for annuloplasty ring and over-wire rotation tool," filed May 4, 2010, which published as WO 2010/128503.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, comprising:
an implant comprising:
a tissue-adjusting member configured to be coupled to cardiovascular tissue of a patient, the tissue-adjusting member comprising a longitudinal member; and
a tissue anchor coupled to the tissue-adjusting member, wherein the tissue anchor comprises a helical shape configured to be screwed into the cardiovascular tissue of the patient;
a tissue-coupling element coupled to the longitudinal member; and
a delivery tool reversibly couplable to the implant, the delivery tool being configured to cardiovascular deliver the implant to the cardiovascular tissue of the patient, the delivery tool comprising:
a handle;
an elongate shaft, extending distally away from the handle;
a tissue-coupling-element holder coupled to a portion of the elongate shaft distal from the handle, the delivery tool being configured to deliver the implant endovascularly to the cardiovascular tissue while the handle is outside the patient and the tissue-coupling-element holder, disposed proximally from the tissue anchor, holds the tissue coupling element; and
an actuating element configured to screw the tissue anchor into the cardiovascular tissue by rotating the tissue anchor about an axis of rotation that is along a longitudinal axis of the delivery tool while not rotating the tissue-coupling-element holder with respect to the shaft.

2. The apparatus according to claim 1, wherein the tissue-adjusting member comprises one or more artificial chordae tendineae.

3. The apparatus according to claim 1, wherein the tissue-coupling-element holder surrounds the portion of the elongate shaft.

4. The apparatus according to claim 1, wherein the tissue-coupling-element holder is coupled to the portion of the elongate shaft in a manner in which pulling the tissue-coupling-element holder proximally facilitates pulling of the elongate shaft proximally.

5. The apparatus according to claim 1, wherein the tissue-coupling-element holder is shaped so as to define a planar element.

6. The apparatus according to claim 1, where the tissue-coupling element comprises a needle, and wherein the tissue-coupling-element holder is shaped so as to define a slit for reversibly coupling the tissue-coupling element to the tissue-coupling-element holder.

7. The apparatus according to claim 1, wherein the elongate shaft comprises a multi-lumen elongate shaft, and wherein, during the delivery of the implant to the cardiovascular tissue of the patient, the longitudinal member is disposed within a secondary lumen of the multi-lumen elongate shaft.

8. The apparatus according to claim 7, wherein the secondary lumen is shaped so as to define a slit that runs parallel to a longitudinal axis of the delivery tool, and wherein the longitudinal member is pullable away from the longitudinal axis of the delivery tool via the slit in order to remove the longitudinal member from within the elongate shaft.

9. The apparatus according to claim 1, wherein during the anchoring of the cardiovascular tissue anchor into the tissue of the patient, the tissue-coupling-element holder is configured to be accessible from outside of a body of the patient.

10. A method, comprising:
using a delivery tool, advancing an implant endovascularly to cardiovascular tissue and delivering the implant to cardiovascular tissue, the implant including (1) a tissue-adjusting member including a longitudinal member, and (2) a tissue anchor coupled to the tissue-adjusting member, the tissue anchor comprising a helical shape configured to be screwed into the cardiovascular tissue, the tissue-adjusting member being coupled to a tissue-coupling element, the delivery tool including:
a handle;
an elongate shaft, extending distally away from the handle;
a tissue-coupling-element holder coupled to a distal portion of the elongate shaft, the tissue-coupling-element holder being configured to hold the tissue-coupling element during the delivering of the implant to the cardiovascular tissue; and
an actuating element configured to rotate the tissue anchor about an axis of rotation that is along a longitudinal axis of the delivery tool
screwing the tissue anchor into the cardiovascular tissue by rotating the tissue anchor about the axis of rotation by rotating the actuating element of the delivery tool while not rotating the tissue-coupling-element holder with respect to the shaft.

11. The method according to claim 10, wherein the tissue-adjusting member includes one or more artificial chordae tendineae.

12. The method according to claim 10, wherein the tissue-coupling-element holder surrounds the portion of the elongate shaft.

13. The method according to claim 10, further comprising pulling of the elongate shaft proximally by pulling the tissue-coupling-element holder proximally.

14. The method according to claim 10, wherein during the anchoring of the tissue anchor into the cardiovascular tissue, the tissue-coupling-element holder is configured to be accessible from outside of a body of a patient, and wherein the method comprises accessing the tissue-coupling-element holder from outside the body of the patient.

15. The method according to claim 10, further comprising:
- subsequently to the anchoring of the tissue anchor into the cardiovascular tissue, suturing the longitudinal member to the cardiovascular tissue using the tissue-coupling element; and
- subsequently to the suturing, clipping the longitudinal member and removing from a body of a patient (a) excess portions of the longitudinal member, and (b) the tissue-coupling element.

16. The method according to claim 10, where the tissue-coupling element includes a needle, wherein the tissue-coupling-element holder is shaped so as to define a slit for reversibly coupling the tissue-coupling element to the tissue-coupling-element holder, and wherein the method further comprises decoupling the needle from the slit of the tissue-coupling-element holder subsequently to the delivering of the implant.

17. The method according to claim 16, further comprising, subsequently to the decoupling of the needle from the slit, suturing the longitudinal member to the cardiovascular tissue using the needle.

18. The method according to claim 10, wherein the elongate shaft comprises a multi-lumen elongate shaft, and wherein, during the delivering of the implant to the cardiovascular tissue, the longitudinal member is disposed within a secondary lumen of the multi-lumen elongate shaft.

19. The method according to claim 18, wherein the secondary lumen is shaped so as to define a slit that runs parallel to a longitudinal axis of the delivery tool, and wherein the method further comprises removing the longitudinal member from within the elongate shaft by pulling the longitudinal member away from the longitudinal axis of the delivery tool via the slit.

* * * * *